Figure 1:
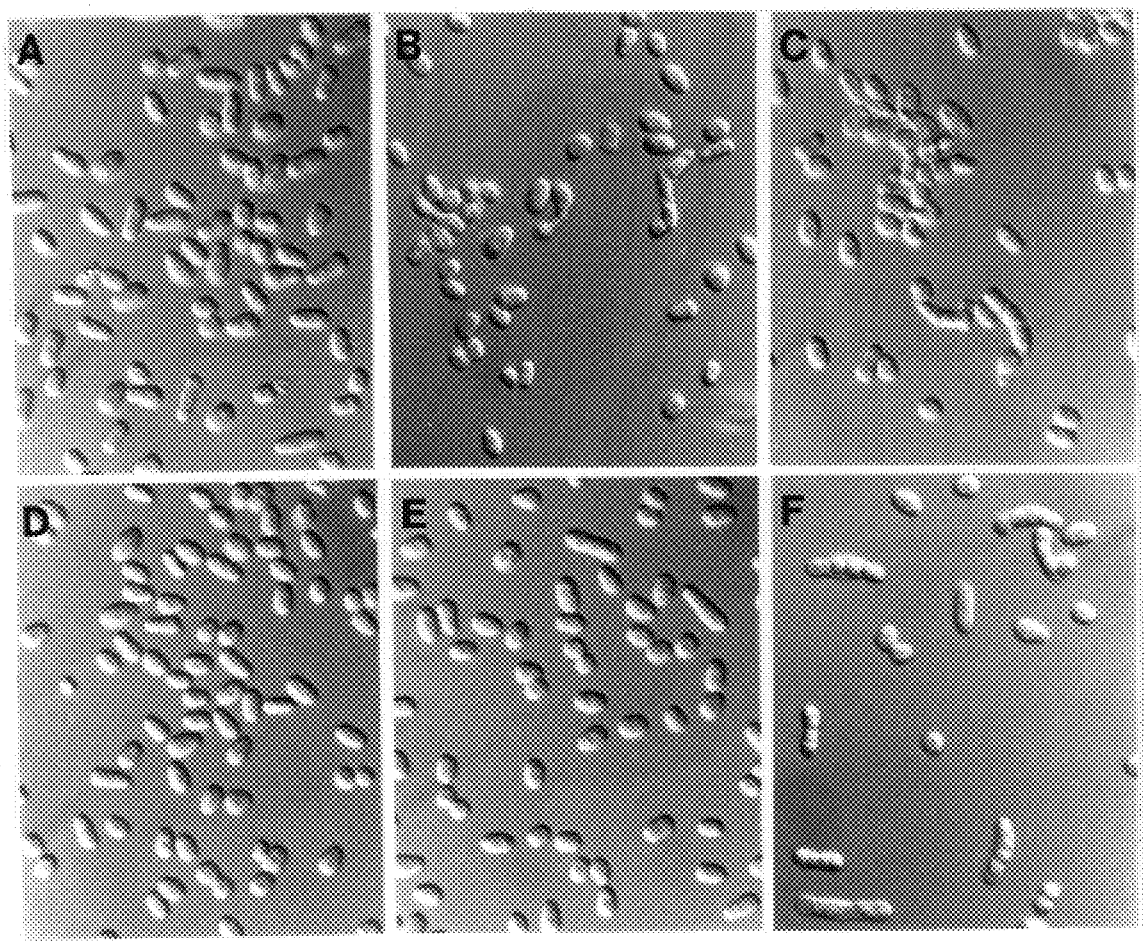

United States Patent [19]
Marshall et al.

[11] Patent Number: 5,958,721
[45] Date of Patent: Sep. 28, 1999

[54] METHODS FOR SCREENING OF SUBSTANCES FOR THERAPEUTIC ACTIVITY AND YEAST FOR USE THEREIN

[75] Inventors: Christopher John Marshall, Purley; Alan Ashworth; David Anthony Hughes, both of London, all of United Kingdom

[73] Assignee: Cancer Research Campaign Technology, Ltd., London, United Kingdom

[21] Appl. No.: 08/530,290

[22] PCT Filed: Mar. 31, 1994

[86] PCT No.: PCT/GB94/00694

§ 371 Date: Dec. 14, 1995

§ 102(e) Date: Dec. 14, 1995

[87] PCT Pub. No.: WO94/23039

PCT Pub. Date: Oct. 13, 1994

[30] Foreign Application Priority Data

Apr. 7, 1993 [GB] United Kingdom ............... 9307250
Feb. 10, 1994 [GB] United Kingdom ............... 9402573

[51] Int. Cl.$^6$ ............................. C12N 1/19; C12Q 1/02
[52] U.S. Cl. ................. 435/29; 435/254.2; 435/254.21
[58] Field of Search ......................... 435/4, 29, 69.1, 435/172.1, 172.3, 194, 196, 254.2, 254.21, 483; 514/1

[56] References Cited

U.S. PATENT DOCUMENTS 4,980,281 12/1990 Housey ................................ 435/29

OTHER PUBLICATIONS

Entry 4281 "Genistein" in The Merck Index, Merck & Co., Inc., p. 686, 1989.
Gotoh et al. Okadaic acid activates microtubule–associated protein kinase in quiescent fibroblastic cells. Eur. J. Biochem. 193(3):671–4, Nov. 1990.
Luckas. Phycotoxins in seafood–toxicological and chromatographic aspects. J. Chromatog. 624: 439–456, 1992.
Torres et al. Stimulation of human neutophils with formyl–methionyl–leucyl–phenylalinine induces tyrosine phosphorylation and activation of two distinct mitogen–activated protein kinases. J. Immunol. 150(4): 1563–1578, Feb. 1993.
Schweigerer et al. Identification in human urine of a natural growth inhibitor for cells derived from solid paediatric tumors. Eur. J. Clin. Inv. 22(4): 260–264, Apr. 1992.
Cohen, Phillip, et al. (1990) "Okadaic Acid: a new probe for the study of cellular regulation", TIBS 15:98–102.

Hughes, David A., et al. (1993) "Complementation of byr1 in fission yeast by mammalian MAP kinase kinase requires coexpression of Raf kinase", Nature, 364:349–352.
Sun, Hong, et al. (1993) "MKP–1 (3CH134), an Immediate Early Gene Product, is a Dual Specificity Phosphatase That Dephosphorylates MAP Kinase In Vivo", Cell, 75:487–493.
Charles, Catherine H., et al. (1992) "cDNA sequence of a growth factor–inducible immediate early gene and characterization of its encoded protein", Oncogene 7:187–190.
Kyriakis, John M., et al. (1992) "Raf–1 activates MAP kinase–kinase", Nature, 358:417–421.
Styrkarsdottir, Unnur, et al. (1992) "Functional conservation between Schizosaccharomyces pombe ste8 and Saccharomyces cerevisiae STE11 protein kinases in yeast signal transduction", Mol Gen Genet, 235:122–130.
Nadin–Davis, Susan A., et al. (1988) "A gene which encodes a predicted protein kinase can restore some functions of the ras gene in fission yeast", EMBO Journal, 7(4):985–993.
Lee, Kyung S., et al. (1993) "A Yeast Mitogen–Activated Protein Kinase Homolog (Mpklp) Mediates Signalling by Protein Kinase C", Molecular and Cellular Biology, 13(5):3067–3075.
Gotoh, Yukiko, et al. (1993) "Schizosaccharomyces pombe Spk1 is a Tyrosine–Phosophorylated Protein Functionally Related to Xenopus Mitogen–Activated Protein Kinase", Molecular and Cellular Biology, 13(10):6427–6434.
Neiman, Aaron M., (1993) "Functional Homology of Protein Kinases Required for Sexual Differentiation in Schizosaccharomyces pombe and Saccharomyces cerevisiae Suggests a Conserved Signal Transduction Module in Eukaryotic Organisms", Molecular Biology of the Cell, 4:107–120.
Kyriakis, John M., et al. (1992) "Raf–1 activates MAP kinase–kinase", Nature, 358:417–421.
Dent, Paul, et al. (1992) "Activation of Mitogen–Activated Protein Kinase Kinase by v-Raf in NIH 3T3 Cells and in Vitro", Science, 257:1404–1407.

Primary Examiner—George C. Elliott
Assistant Examiner—Thomas G. Larson
Attorney, Agent, or Firm—Townsend and Townsend and Crew

[57] ABSTRACT

Methods of screening for substances which affect mammalian MAP kinase pathways, both inhibitors and activators, are provided. Substances identified using the methods as having such an effect are candidate pharmaceuticals for use in treatment of cancer, inflammatory disorders, cardiovascular disorders or neurological disease. Yeasts are provided for use in the methods. In the yeast, deficiencies in yeast MAPKK kinase and MAPK kinase are complemented by mammalian MAPKK kinase and MAPK kinase. Yeast MAPK may also be replaced with a mammalian homologue and mammalian MAPK phosphatases may be introduced.

39 Claims, 10 Drawing Sheets

```
ATC CTT CCC TCC CTC TAC CTT GGA AGT GCC TAC CAT GCA TCC AAG
TGC GAG TTC CTG GCC AAC TTG CAC ATC ACA GCC CTG CTG AAT GTC
TCC CGA CGG ACC TCC GAG GCC TGC ATG ACC CAC CTA CAC TAC AAA
TGG ATC CCT GTG GAA GAC AGC CAC ACG GCT GAC ATT AGC TCC CAC
TTT CAA GAA GCA ATA GAC TTC ATT GAC TGT GTC AGG GAA AAG GGA
GGC AAG GTC CTG
```

Fig. 6A.

```
ATC CTT CCC TTC CTC TAC CAT GCT AGT GCC TAC CAT GCT GCC CGG
AGA GAC ATG CTG GAC GCC CTG GGC ATC ACG GCT CTG TTG AAT GTC
TCC TCG GAC TGC CCA AAC CAC TTT GAA GGA CAC TAT CAG TAC AAG
TGC ATC CCA GTG GAA GAT AAC CAC AAG GCC GAC ATC AGC TCC TGG
TTC ATG GAA GCC ATA GAG TAC ATC GAT GCC GTG AAG GAC TGC CGT
GGG CGC GTG CTG
```

Fig. 6B.

```
CCG ATA AGA TTC CTC TAT CTT CTA AAG CTT TAC TCT CCC CGA AAA
GTC CTC TAC CGC TCC TCC GCC CGG CTC CTC GGT CTG AAG ACA CCG
AGA CTC GAC CAG ACT CGC CAA CTC
```

Fig. 6C.

```
ATC TTG CCC TAC CTG TTC CTG GGC AGC TGC AGT CAC TCG TCA GAC
CTG CAG GGG CTG CAG GCC TGT GGC ATC ACA GCC GTC CTC AAC GTG
TCC GCC AGC TGC CCC AAC CAC TTT GAG GGC CTT TTC CGC TAC AAG
AGT ATC CCT GTG GAG GAC AAC CAG ATG GTG GAG ATC AGT GCC TGG
TTC CAG GAG GCC ATA GGC TTC ATT GAC TGG GTG AAG AAC AGC GGA
GGC CGG GTG CTG
```

Fig. 6D.

```
GCT GAC ATT AGC TCC CAC TTT CAA GAA GCA ATT GAT TTT ATT GAC
TGC GTC AGG GAA GGA GGA GGC AAG GTC CTA GTC CAC TGT GAG GCT
GGG GTC TCG AGG TCA CCC ACC ATC TGC ATG GCG TAC CTC ATG AAG
ACC AAG CAG TTC CGC CTG AAG GAG GCC TTC GAC ATC GTC AAG CAG
AGG AGG AGC GTG ATC TCT CCC AAC TTT GGC TTT ATG
```

Fig. 6E.

```
TCTTGAGAGC TGTGTGGTCG CCATGCTGTC CCCTGAAGCG AGGTGATGCG
GTACCTGGTC GAAGTGGAGG AGCTGGCCGA GGCGGTGCTG TCGGACAAGC
GGACGATTGT AGACCTGGAT ACCAAGAGGA AT
```

Fig. 6F.

```
CCCGGGTTCT CTTCTCTTCC TCGCGCGCCC AGCCGCCTCG GTTCCCGGCG
ACCATGGTGA CGATGGAGGA GCTGCGGGAG ATGGACTGCA GTGTGCTCAA
AAGGCTGATG AACCGGGACG AGAATGGCGG CGGCGCGGGC GGCAGCGGCA
GCCACGGCAC CCTGGGGCTG CCGAGCGGCG GCAAGTGCCT GCTGCTGGAC
TGCAGACCGT TCCTGGCGCA CAGCGCGGGC TACATCCTAG GTTCGGTCAA
CGTGCGCTGT AACACCATCG TGCGGCGGCG GGCTAAGGGC TCCGTGAGCC
TGGAGCAGAT CCTGCCCGCC GAGGAGGAGG TACGCGCCCG CTTGCGCTCC
GGCCTCTACT CGGCGGTCAT CGTCTACGAC GAGCGCAGCC CGCGCGCCGA
GAGCCTCCGC GAGGACAGCA CCGTGTCGCT GGTGGTGCAG GCGCTGCGCC
GCAACGCCGA GCGCACCGAC ATCTGCCTGC TCAAAGGCGG CTATGAGAGG
TTTTCCTCCG AGTACCCAGA ATTCTGTTCT AAAACCAAGG CCCTGGCAGC
CATCCCACCC CCGGTTCCCC CCAGCGCCAC AGAGCCCTTG GACCTGGACT
GCAGCTCCTG TGGGACCCCA CTACACGACC AGGAGGGTCC TGTGGAGATC
CTTCCCTTCC TCTACCTCGG CAGTGCCTAC CATGCTGCCC GGAGAGACAT
GCTGGACGCC CTGGGCATCA CGGCTCTGTT GAATGTCTCC TCGGACTGCC
CAAACCACTT TGAAGGACAC TATCAGTACA AGTGCATCCC AGTGGAAGAT
AACCACAAGG CCGACATCAG CTCCTGGTTC ATGGAAGCCA TAGAGTACAT
CGATGCCGTG AAGGACTGCC GTGGGCGCGT GCTGGTGCAC TGCCAGGCGG
GCATCTCGCG GTCGGCCACC ATCTGCCTGG CCTACCTGAT GATGAAGAAA
CGGGTGAGGC TGGAGGAGGC CTTCGAGTTC GTTAAGCAGC GCCGCAGCAT
CATCTCGCCC AACTTCAGCT TCATGGGGCA GCTGCTGCAG TTCGAGTCCC
AGGTGCTGGC CACGTCCTGT GCTGCGGAGG CTGCTAGCCC CTCGGGACCC
CTGCGGGAGC GGGGCAAGAC CCCCGCCACC CCCACCTCGC AGTTCGTCTT
CAGCTTTCCG GTCTCCGTGG GCGTGCACTC GGCCCCAGC AGCCTGCCCT
ACCTGCACAG CCCCATCACC ACCTCTCCCA GCTGTTAG
```

Fig. 6G.

ATC CTT GTG GAA GAA GGC CAC ATG GCT GAC ATT AGC TCT CAC TTT
CAA GAA GCA ATA GAC TTC ATT GAC TGT GTC AGA GAA AAG AAA GGC
AAG GTC CTG GTC CAC TGT GAA GCT GGG TTC TCC TGT TCA CCC ACC

Fig. 6H.

AAAGAGTTGT CTACACAGGC ATATATGATA CAGAAGGTGT AGCTCCTACC
AAAAGTGGAG AGCGACAACC CATCCAGATC ACCATGCCGT TCACAGACAT
TGGGACCTTC GAGACAGTGT GGCAAGTCAA GTTCTACAAT TACCACAAGC
GAGACCATTG CCAGTGGGGA AG

Fig. 6I.

```
CL100   I L P F L Y L G S A Y H A S R K D M L D A L G I T A L I
STY2                    L C E F     A N     H           L
STY3                        A A R                       L
STY4    P I R       L K L   S P R K V L Y R S S A R L L G   K
STY5          Y   F       C S   S   D L Q G   Q   C       V L

CL100   N V S A N C P N H F E G H Y Q Y K S I P V E D N H K A D
STY2        R R T S E A C M T   L H     W           S
STY3        S D                         C
STY4    T P R L D Q T R Q L . . . . . . . . . . . . . . . . . .
STY5        S             L F R                 Q M V E

CL100   I S S W F N E A I D F I D S I K N A G G R V F
STY2        H   Q             C V R E K     K     L
STY3        M         E Y     C V   D C R         L
STY4    . . . . . . . . . . . . . . . . . . . . . . .
STY5        A       Q       G       W V       S     L
```

Fig. 7A.

```
CL100   A D I S S W F N E A I D F I D S I K N A G G R V
STY6          H   Q             C V R E G     K

CL100   F V H C Q A G I S R S A T I C L A Y L M R T N R
STY6    L   E       V     P       M       K   K Q

CL100   V K L D E A F E F V K Q R R S I I S P N F S F M
STY6    F R   K     D I         V                 G
```

Fig. 7B.

```
CL100   I P V E D N H K A D I S S W F N E A I D F I D S
STY9        L   E G   M         H   Q                 C

CL100   I K N A G G R V F V H C Q A G I S R S A T
STY9    V R E K K     K L       E       F   C P
```

Fig. 7C.

```
              10        20        30        40        50        60        70        80        90       100
     1234567890123456789012345678901234567890123456789012345678901234567890123456789012345678901234567890
STY8 MVTMEELREMDCSVKKRLMNRDENGGGAGGSGSHGTLGLPSGGKCLLEDCRPFLAHSAGYILGSVNVRCNTIVRRAKGSVSLEQILPAEEVR-RERSG
CL100 MV-M-EVGTLDAGGERAL-------GER------AAQCLLEDCRSFFAFNAGHIAGSVNVRFSTIVRRRAKGAMGLEHIVPNAE-LRGRILAG 110       120       130       140       150       160       170       180       190       200
     1234567890123456789012345678901234567890123456789012345678901234567890123456789012345678901234567890
STY8 LYSAVIVYDERSPRAESLREDSTVSIVVQALRRNAERTDICLLKGGYERFSSEYPEFCSKTKALAAIPPPVPPSATEPLDLDCSSCGTPLHDQEGPVEIL
CL100 AYHAVVLLDERSAALDGAKRDGTLALAAGALCREARAAQVFFLKGGYEAFSASCPELCSKQSTPMGLSLRLSTSVPDSAESGCSSCSTPLYDQGGPVEIL 210       220       230       240       250       260       270       280       290       300
     1234567890123456789012345678901234567890123456789012345678901234567890123456789012345678901234567890
STY8 PFLYLGSAYHAARRDMLDALGITALLNVSSDCPNHFEGHYQYKCIPVEDNHKADISSWFMEAIEYIDAVKDCRGRVLVHCQAGISRSATICLAYLMKKR
CL100 PFLYLGSAYHASRKDMLDALGITALINVSANCPNHFEGHYQYKSIPVEDNHKADISSWFNEAIDFIDSIKNAGGRVFVHCQAGISRSATICLAYLMRTNR 310       320       330       340       350       360       370       380       390
     123456789012345678901234567890123456789012345678901234567890123456789012345678901234
STY8 VRLEEAFETVKQRRSIISPNFSFMGQLLQFESGVLATSCAAEAASPSGPLRERGKTPATPTSQFVFSFPVSVGVHSAPSSLPYLHSPITTSPSC
CL100 VKLDEAFEFVKQRRSIISPNFSFMGQLLQFESQVLAPHCSAEAGSPAMAVLDRGTSTTT----VTNFPVSIPVHSTNSALSYLQSPITTSPSC
```

Fig. 7D.

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

TAYGAYCARG GDGGNCCWGT DGA      23

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
ATBCCWGCYT GRCARTGNAC                                               20
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Tyr Asp Gln Gly Gly Pro Val Glu
1               5
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Val His Cys Gln Ala Gly Ile
1               5
```

(2) INFORMATION FOR SEQ ID NO:5:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
ATCCTTCCCT CCCTCTACCT TGGAAGTGCC TACCATGCAT CCAAGTGCGA GTTCCTGGCC    60

AACTTGCACA TCACAGCCCT GCTGAATGTC TCCCGACGGA CCTCCGAGGC CTGCATGACC   120

CACCTACACT ACAAATGGAT CCCTGTGGAA GACAGCCACA CGGCTGACAT TAGCTCCCAC   180

TTTCAAGAAG CAATAGACTT CATTGACTGT GTCAGGGAAA AGGGAGGCAA GGTCCTG      237
```

(2) INFORMATION FOR SEQ ID NO:6:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
ATCCTTCCCT TCCTCTACCA TGCTAGTGCC TACCATGCTG CCCGGAGAGA CATGCTGGAC        60

GCCCTGGGCA TCACGGCTCT GTTGAATGTC TCCTCGGACT GCCCAAACCA CTTTGAAGGA       120

CACTATCAGT ACAAGTGCAT CCCAGTGGAA GATAACCACA AGGCCGACAT CAGCTCCTGG       180

TTCATGGAAG CCATAGAGTA CATCGATGCC GTGAAGGACT GCCGTGGGCG CGTGCTG         237
```

(2) INFORMATION FOR SEQ ID NO:7:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
CCGATAAGAT TCCTCTATCT TCTAAAGCTT TACTCTCCCC GAAAAGTCCT CTACCGCTCC        60

TCCGCCCGGC TCCTCGGTCT GAAGACACCG AGACTCGACC AGACTCGCCA ACTC            114
```

(2) INFORMATION FOR SEQ ID NO:8:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
ATCTTGCCCT ACCTGTTCCT GGGCAGCTGC AGTCACTCGT CAGACCTGCA GGGGCTGCAG        60

GCCTGTGGCA TCACAGCCGT CCTCAACGTG TCCGCCAGCT GCCCCAACCA CTTTGAGGGC       120

CTTTTCCGCT ACAAGAGTAT CCCTGTGGAG GACAACCAGA TGGTGGAGAT CAGTGCCTGG       180

TTCCAGGAGG CCATAGGCTT CATTGACTGG GTGAAGAACA GCGGAGGCCG GGTGCTG         237
```

(2) INFORMATION FOR SEQ ID NO:9:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GCTGACATTA GCTCCCACTT TCAAGAAGCA ATTGATTTTA TTGACTGCGT CAGGGAAGGA        60

GGAGGCAAGG TCCTAGTCCA CTGTGAGGCT GGGGTCTCGA GGTCACCCAC CATCTGCATG       120

GCGTACCTCA TGAAGACCAA GCAGTTCCGC CTGAAGGAGG CCTTCGACAT CGTCAAGCAG       180

AGGAGGAGCG TGATCTCTCC CAACTTTGGC TTTATG                                216
```

(2) INFORMATION FOR SEQ ID NO:10:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TCTTGAGAGC TGTGTGGTCG CCATGCTGTC CCCTGAAGCG AGGTGATGCG GTACCTGGTC      60

GAAGTGGAGG AGCTGGCCGA GGCGGTGCTG TCGGACAAGC GGACGATTGT AGACCTGGAT     120

ACCAAGAGGA AT                                                         132
```

(2) INFORMATION FOR SEQ ID NO:11:

(i) SEQUENCE CHARACTERISTICS:
        (A) LENGTH: 1238 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
CCCGGGTTCT CTTCTCTTCC TCGCGCGCCC AGCCGCCTCG GTTCCCGGCG ACCATGGTGA      60

CGATGGAGGA GCTGCGGGAG ATGGACTGCA GTGTGCTCAA AAGGCTGATG AACCGGGACG     120

AGAATGGCGG CGGCGCGGGC GGCAGCGGCA GCCACGGCAC CCTGGGGCTG CCGAGCGGCG     180

GCAAGTGCCT GCTGCTGGAC TGCAGACCGT TCCTGGCGCA CAGCGCGGGC TACATCCTAG     240

GTTCGGTCAA CGTGCGCTGT AACACCATCG TGCGGCGGCG GGCTAAGGGC TCCGTGAGCC     300

TGGAGCAGAT CCTGCCCGCC GAGGAGGAGG TACGCGCCCG CTTGCGCTCC GGCCTCTACT     360

CGGCGGTCAT CGTCTACGAC GAGCGCAGCC CGCGCGCCGA GAGCCTCCGC GAGGACAGCA     420

CCGTGTCGCT GGTGGTGCAG GCGCTGCGCC GCAACGCCGA GCGCACCGAC ATCTGCCTGC     480

TCAAAGGCGG CTATGAGAGG TTTTCCTCCG AGTACCCAGA ATTCTGTTCT AAAACCAAGG     540

CCCTGGCAGC CATCCCACCC CCGGTTCCCC CCAGCGCCAC AGAGCCCTTG GACCTGGACT     600

GCAGCTCCTG TGGGACCCCA CTACACGACC AGGAGGGTCC TGTGGAGATC CTTCCCTTCC     660

TCTACCTCGG CAGTGCCTAC CATGCTGCCC GGAGAGACAT GCTGGACGCC CTGGGCATCA     720

CGGCTCTGTT GAATGTCTCC TCGGACTGCC CAAACCACTT TGAAGGACAC TATCAGTACA     780

AGTGCATCCC AGTGGAAGAT AACCACAAGG CCGACATCAG CTCCTGGTTC ATGGAAGCCA     840

TAGAGTACAT CGATGCCGTG AAGGACTGCC GTGGGCGCGT GCTGGTGCAC TGCCAGGCGG     900

GCATCTCGCG GTCGGCCACC ATCTGCCTGG CCTACCTGAT GATGAAGAAA CGGGTGAGGC     960

TGGAGGAGGC CTTCGAGTTC GTTAAGCAGC GCCGCAGCAT CATCTCGCCC AACTTCAGCT    1020

TCATGGGGCA GCTGCTGCAG TTCGAGTCCC AGGTGCTGGC CACGTCCTGT GCTGCGGAGG    1080

CTGCTAGCCC CTCGGGACCC CTGCGGGAGC GGGGCAAGAC CCCCGCCACC CCCACCTCGC    1140

AGTTCGTCTT CAGCTTTCCG GTCTCCGTGG GCGTGCACTC GGCCCCAGC AGCCTGCCCT    1200

ACCTGCACAG CCCCATCACC ACCTCTCCCA GCTGTTAG                            1238
```

(2) INFORMATION FOR SEQ ID NO:12:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
ATCCTTGTGG AAGAAGGCCA CATGGCTGAC ATTAGCTCTC ACTTTCAAGA AGCAATAGAC      60

TTCATTGACT GTGTCAGAGA AAAGAAAGGC AAGGTCCTGG TCCACTGTGA AGCTGGGTTC     120

TCCTGTTCAC CCACC                                                      135
```

(2) INFORMATION FOR SEQ ID NO:13:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
AAAGAGTTGT CTACACAGGC ATATATGATA CAGAAGGTGT AGCTCCTACC AAAAGTGGAG      60

AGCGACAACC CATCCAGATC ACCATGCCGT TCACAGACAT TGGGACCTTC GAGACAGTGT     120

GGCAAGTCAA GTTCTACAAT TACCACAAGC GAGACCATTG CCAGTGGGGA AG            172
```

(2) INFORMATION FOR SEQ ID NO:14:

(i) SEQUENCE CHARACTERISTICS:
        (A) LENGTH: 79 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Ile Leu Pro Phe Leu Tyr Leu Gly Ser Ala Tyr His Ala Ser Arg Lys
1               5                   10                  15

Asp Met Leu Asp Ala Leu Gly Ile Thr Ala Leu Ile Asn Val Ser Ala
            20                  25                  30

Asn Cys Pro Asn His Phe Glu Gly His Tyr Gln Tyr Lys Ser Ile Pro
        35                  40                  45

Val Glu Asp Asn His Lys Ala Asp Ile Ser Ser Trp Phe Asn Glu Ala
    50                  55                  60

Ile Asp Phe Ile Asp Ser Ile Lys Asn Ala Gly Gly Arg Val Phe
65                  70                  75
```

(2) INFORMATION FOR SEQ ID NO:15:

(i) SEQUENCE CHARACTERISTICS:
        (A) LENGTH: 79 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Ile Leu Pro Phe Leu Tyr Leu Gly Ser Ala Tyr His Ala Ser Leu Cys
1               5                   10                  15

Glu Phe Leu Ala Asn Leu His Ile Thr Ala Leu Leu Asn Val Ser Arg
            20                  25                  30

Arg Thr Ser Glu Ala Cys Met Thr His Leu His Tyr Lys Trp Ile Pro
        35                  40                  45

Val Glu Asp Ser His Lys Ala Asp Ile Ser Ser His Phe Gln Glu Ala
    50                  55                  60

Ile Asp Phe Ile Asp Cys Val Arg Glu Lys Gly Gly Lys Val Leu
65                  70                  75
```

(2) INFORMATION FOR SEQ ID NO:16:

(i) SEQUENCE CHARACTERISTICS:
        (A) LENGTH: 79 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:16:

```
Ile Leu Pro Phe Leu Tyr Leu Gly Ser Ala Tyr His Ala Ala Arg
1               5                  10                 15

Asp Met Leu Asp Ala Leu Gly Ile Thr Ala Leu Leu Asn Val Ser Ser
            20                  25                  30

Asp Cys Pro Asn His Phe Glu Gly His Tyr Gln Tyr Lys Cys Ile Pro
            35                  40                  45

Val Glu Asp Asn His Lys Ala Asp Ile Ser Ser Trp Phe Met Glu Ala
50                  55                  60

Ile Glu Tyr Ile Asp Cys Val Lys Asp Cys Arg Gly Arg Val Leu
65                  70                  75
```

(2) INFORMATION FOR SEQ ID NO:17:

(i) SEQUENCE CHARACTERISTICS:
(A) LENGTH: 38 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:17:

```
Pro Ile Arg Phe Leu Tyr Leu Leu Lys Leu Tyr Ser Pro Arg Lys Val
1               5                  10                 15

Leu Tyr Arg Ser Ser Ala Arg Leu Leu Gly Leu Lys Thr Pro Arg Leu
            20                  25                  30

Asp Gln Thr Arg Gln Leu
            35
```

(2) INFORMATION FOR SEQ ID NO:18:

(i) SEQUENCE CHARACTERISTICS:
(A) LENGTH: 79 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:18:

```
Ile Leu Pro Tyr Leu Phe Leu Gly Ser Cys Ser His Ser Ser Asp Leu
1               5                  10                 15

Gln Gly Leu Gln Ala Cys Gly Ile Thr Ala Val Leu Asn Val Ser Ala
            20                  25                  30

Ser Cys Pro Asn His Phe Glu Gly Leu Phe Arg Tyr Lys Ser Ile Pro
            35                  40                  45

Val Glu Asp Asn Gln Met Val Glu Ile Ser Ala Trp Phe Gln Glu Ala
50                  55                  60

Ile Gly Phe Ile Asp Trp Val Lys Asn Ser Gly Gly Arg Val Leu
65                  70                  75
```

(2) INFORMATION FOR SEQ ID NO:19:

(i) SEQUENCE CHARACTERISTICS:
(A) LENGTH: 72 amino acids
(B) TYPE: amino acid
(C) STRANDEDNESS:

(D) TOPOLOGY: linear (ii) MOLECULE TYPE: peptide (xi) SEQUENCE DESCRIPTION: SEQ ID NO:19:

Ala Asp Ile Ser Ser Trp Phe Asn Glu Ala Ile Asp Phe Ile Asp Ser
1               5                   10                  15

Ile Lys Asn Ala Gly Gly Arg Val Phe Val His Cys Gln Ala Gly Ile
            20                  25                  30

Ser Arg Ser Ala Thr Ile Cys Leu Ala Tyr Leu Met Arg Thr Asn Arg
        35                  40                  45

Val Lys Leu Asp Glu Ala Phe Glu Phe Val Lys Gln Arg Arg Ser Ile
    50                  55                  60

Ile Ser Pro Asn Phe Ser Phe Met
65                  70

(2) INFORMATION FOR SEQ ID NO:20:

(i) SEQUENCE CHARACTERISTICS:
        (A) LENGTH: 72 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Ala Asp Ile Ser Ser His Phe Gln Glu Ala Ile Asp Phe Ile Asp Cys
1               5                   10                  15

Val Arg Glu Gly Gly Gly Lys Val Leu Val His Cys Glu Ala Gly Val
            20                  25                  30

Ser Arg Ser Pro Thr Ile Cys Met Ala Tyr Leu Met Lys Thr Lys Gln
        35                  40                  45

Phe Arg Leu Lys Glu Ala Phe Asp Ile Val Lys Gln Arg Arg Ser Val
    50                  55                  60

Ile Ser Pro Asn Phe Gly Phe Met
65                  70

(2) INFORMATION FOR SEQ ID NO:21:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Ile Pro Val Glu Asp Asn His Lys Ala Asp Ile Ser Ser Trp Phe Asn
1               5                   10                  15

Glu Ala Ile Asp Phe Ile Asp Ser Ile Lys Asn Ala Gly Gly Arg Val
            20                  25                  30

Phe Val His Cys Gln Ala Gly Ile Ser Arg Ser Ala Thr
        35                  40                  45

(2) INFORMATION FOR SEQ ID NO:22:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Ile Leu Val Glu Glu Gly His Met Ala Asp Ile Ser Ser His Phe Gln
1               5                   10                  15

Glu Ala Ile Asp Phe Ile Asp Cys Val Arg Glu Lys Lys Gly Lys Val
                20                  25                  30

Leu Val His Cys Glu Ala Gly Phe Ser Cys Ser Pro Thr
                35                  40                  45

(2) INFORMATION FOR SEQ ID NO:23:

(i) SEQUENCE CHARACTERISTICS:
        (A) LENGTH: 394 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Met Val Thr Met Glu Glu Leu Arg Glu Met Asp Cys Ser Val Leu Lys
1               5                   10                  15

Arg Leu Met Asn Arg Asp Glu Asn Gly Gly Gly Ala Gly Gly Ser Gly
                20                  25                  30

Ser His Gly Thr Leu Gly Leu Pro Ser Gly Gly Lys Cys Leu Leu Leu
                35                  40                  45

Asp Cys Arg Pro Phe Leu Ala His Ser Ala Gly Tyr Ile Leu Gly Ser
        50                  55                  60

Val Asn Val Arg Cys Asn Thr Ile Val Arg Arg Ala Lys Gly Ser
65                  70                  75                  80

Val Ser Leu Glu Gln Ile Leu Pro Ala Glu Glu Val Arg Ala Arg
                85                  90                  95

Leu Arg Ser Gly Leu Tyr Ser Ala Val Ile Val Tyr Asp Glu Arg Ser
                100                 105                 110

Pro Arg Ala Glu Ser Leu Arg Glu Asp Ser Thr Val Ser Leu Val Val
                115                 120                 125

Gln Ala Leu Arg Arg Asn Ala Glu Arg Thr Asp Ile Cys Leu Leu Lys
130                 135                 140

Gly Gly Tyr Glu Arg Phe Ser Ser Glu Tyr Pro Glu Phe Cys Ser Lys
145                 150                 155                 160

Thr Lys Ala Leu Ala Ala Ile Pro Pro Val Pro Pro Ser Ala Thr
                165                 170                 175

Glu Pro Leu Asp Leu Asp Cys Ser Ser Cys Gly Thr Pro Leu His Asp
                180                 185                 190

Gln Glu Gly Pro Val Glu Ile Leu Pro Phe Leu Tyr Leu Gly Ser Ala
                195                 200                 205

Tyr His Ala Ala Arg Arg Asp Met Leu Asp Ala Leu Gly Ile Thr Ala
                210                 215                 220

Leu Leu Asn Val Ser Ser Asp Cys Pro Asn His Phe Glu Gly His Tyr
225                 230                 235                 240

Gln Tyr Lys Cys Ile Pro Val Glu Asp Asn His Lys Ala Asp Ile Ser
                245                 250                 255

Ser Trp Phe Met Glu Ala Ile Glu Tyr Ile Asp Ala Val Lys Asp Cys
                260                 265                 270

Arg Gly Arg Val Leu Val His Cys Gln Ala Gly Ile Ser Arg Ser Ala
                275                 280                 285

-continued

```
Thr Ile Cys Leu Ala Tyr Leu Met Met Lys Lys Arg Val Arg Leu Glu
    290                 295                 300

Glu Ala Phe Glu Phe Val Lys Gln Arg Arg Ser Ile Ile Ser Pro Asn
305                 310                 315                 320

Phe Ser Phe Met Gly Gln Leu Leu Gln Phe Ser Gln Val Leu Ala
                325                 330                 335

Thr Ser Cys Ala Ala Glu Ala Ala Ser Pro Ser Gly Pro Leu Arg Glu
                340                 345                 350

Arg Gly Lys Thr Pro Ala Thr Pro Thr Ser Gln Phe Val Phe Ser Phe
            355                 360                 365

Pro Val Ser Val Gly Val His Ser Ala Pro Ser Ser Leu Pro Tyr Leu
370                 375                 380

His Ser Pro Ile Thr Thr Ser Pro Ser Cys
385                 390
```

(2) INFORMATION FOR SEQ ID NO:24:

(i) SEQUENCE CHARACTERISTICS:
        (A) LENGTH: 367 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

```
Met Val Met Glu Val Gly Thr Leu Asp Ala Gly Gly Leu Arg Ala Leu
1               5                   10                  15

Leu Gly Glu Arg Ala Ala Gln Cys Leu Leu Leu Asp Cys Arg Ser Phe
                20                  25                  30

Phe Ala Phe Asn Ala Gly His Ile Ala Gly Ser Val Asn Val Arg Phe
            35                  40                  45

Ser Thr Ile Val Arg Arg Arg Ala Lys Gly Ala Met Gly Leu Glu His
        50                  55                  60

Ile Val Pro Asn Ala Glu Leu Arg Gly Arg Leu Leu Ala Gly Ala Tyr
65                  70                  75                  80

His Ala Val Val Leu Leu Asp Glu Arg Ser Ala Ala Leu Asp Gly Ala
                85                  90                  95

Lys Arg Asp Gly Thr Leu Ala Leu Ala Ala Gly Ala Leu Cys Arg Glu
                100                 105                 110

Ala Arg Ala Ala Gln Val Phe Phe Leu Lys Gly Gly Tyr Glu Ala Phe
            115                 120                 125

Ser Ala Ser Cys Pro Glu Leu Cys Ser Lys Gln Ser Thr Pro Met Gly
        130                 135                 140

Leu Ser Leu Pro Leu Ser Thr Ser Val Pro Asp Ser Ala Glu Ser Gly
145                 150                 155                 160

Cys Ser Ser Cys Ser Thr Pro Leu Tyr Asp Gln Gly Gly Pro Val Glu
                165                 170                 175

Ile Leu Pro Phe Leu Tyr Leu Gly Ser Ala Tyr His Ala Ser Arg Lys
                180                 185                 190

Asp Met Leu Asp Ala Leu Gly Ile Thr Ala Leu Ile Asn Val Ser Ala
            195                 200                 205

Asn Cys Pro Asn His Phe Glu Gly His Tyr Gln Tyr Lys Ser Ile Pro
        210                 215                 220

Val Glu Asp Asn His Lys Ala Asp Ile Ser Ser Trp Phe Asn Glu Ala
225                 230                 235                 240

Ile Asp Phe Ile Asp Ser Ile Lys Asn Ala Gly Gly Arg Val Phe Val
```

-continued

```
                            245                 250                 255
His Cys Gln Ala Gly Ile Ser Arg Ser Ala Thr Ile Cys Leu Ala Tyr
            260                 265                 270

Leu Met Arg Thr Asn Arg Val Lys Leu Asp Glu Ala Phe Glu Phe Val
            275                 280                 285

Lys Gln Arg Arg Ser Ile Ile Ser Pro Asn Phe Ser Phe Met Gly Gln
    290                 295                 300

Leu Leu Gln Phe Glu Ser Gln Val Leu Ala Pro His Cys Ser Ala Glu
305                 310                 315                 320

Ala Gly Ser Pro Ala Met Ala Val Leu Asp Arg Gly Thr Ser Thr Thr
                325                 330                 335

Thr Val Phe Asn Phe Pro Val Ser Ile Pro Val His Ser Thr Asn Ser
            340                 345                 350

Ala Leu Ser Tyr Leu Gln Ser Pro Ile Thr Thr Ser Pro Ser Cys
            355                 360                 365
```

METHODS FOR SCREENING OF SUBSTANCES FOR THERAPEUTIC ACTIVITY AND YEAST FOR USE THEREIN

This is a national phase filing of application PCT/GB94/00694, which was filed Mar. 31, 1994.

This invention relates to the screening of candidate substances for potential as pharmaceutical agents. More particularly, it provides a method by which test substances can be screened for their ability to affect a MAP kinase pathway in mammals. Methods are provided for screening test substances for inhibition or activation of the pathway. The invention also provides yeast which are of use in the methods.

It is well known that pharmaceutical research leading to the identification of a new drug generally involves the screening of very large numbers of candidate substances, both before, and even after, a lead compound has been found. This is one factor which makes pharmaceutical research very expensive and time-consuming, so that a method for assisting in the screening process can have considerable commercial importance and utility.

In mammalian cells the activation of the enzyme MAP kinase (MAPK) is a consequence of growth factor stimulation, and is a requirement for cell proliferation (61). Since oncogenic p21 ras proteins transform cells, and inhibition of the normal p21 ras proteins in cells interferes with growth factor signalling, it has been generally assumed that these proteins are involved in the control of cell proliferation. In particular it appears that they are involved in transmitting signals from growth factor receptors to cytoplasmic signal transduction pathways, since both tyrosine kinase-type growth factor receptors and non-tyrosine kinase growth factor receptors require normal p21 ras functions to stimulate MAPK activity and cell proliferation. It seems, therefore, that oncogenic forms of p21 ras uncouple the activation of MAPK from the requirement for external growth factor signals.

It has also been found that the activation of intracellular protein kinase C (PKC) by phorbol esters stimulates MAPK activity without normal ras function in some cell types. It has further been shown that oncogenic p21 Ras introduced into quiescent 3T3 cells rapidly activates PKC and leads to the activation of MAPK in the absence of any external stimuli.

It seemed to us that the activation of MAPK from ras or PKC proceeds successively via the Raf protein kinase and MAPK kinase (MAPKK), essentially along the lines:

It should be noted that there is a family of MAP-kinases and that the pathway is implicated in many diverse cell types [35–37]. Two forms of MAP kinase have been purified from fibroblasts with molecular weights $P42^{mapk}$ and $P44^{mapk}$, (ERK-2 and -1 respectively), [38]. Activation requires an ordered phosphorylation of a threonine and tyrosine located within the conserved kinase subdomain 8, (T183, Y185), [39,40].

Yeast MAPK-pathway homologue proteins are involved in yeast signal transduction, including in response to mating pheromones. In the case of the yeast *Schizosaccharomyces pombe* one MAPK protein is Spk1. Two additional kinases, Byr1 and Byr2, lie in the same pathway as Spk1, of which Byr1 has been shown to have some sequence homology to MAPKK. In addition, the mating pheromone pathway in Spk1 requires Ras protein function, and Byr1 and Byr2 are thought to act downstream of Ras in this pathway. It is possible, therefore that the way in which ras is coupled to these kinase cascades is similar in fission yeast and higher eukaryotes. More particularly, we believe a pathway in *S. pombe* to be essentially of the form:

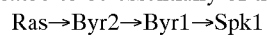

There are equivalent proteins in as follows:

S. pombe S. cerevisiae
  Byr1 (also known as STE1)=STE7
  Byr2 (also known as STE8)=STE11
  Spk1=FUS3/KSS1

Additionally, in *Saccharmyces cerevisiae* there are other pathways with MAP kinase homologues and components with equivalent function to those in the mammlian MAPK pathway: the HOG1 and MPK1 pathways. MPK1 is a yeast MAPK and has the following components in its pathway:

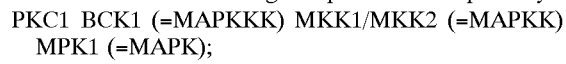

The yeast MAP kinase HOG1 has the following components in its pathway:

In all cases, various additional components may act upstream in response to a stimulus, which may come from outside the organism.

Surprisingly, when we placed a mammalian (human) Raf, or a deletional derivative thereof, together with MAPKK, in a yeast strain deficient in either byr1 or byr2, the engineered strain would mate, indicating that the pathway was functioning, while expression of raf or the raf derivative alone or MAPKK alone did not allow byr1 or byr2 mutant cells to mate. This strongly suggests that Raf can directly phosphorylate and activate MAPKK. It also suggested to us the replacement of spk1 with MAPK and/or yeast ras with mammalian (human) ras in yeast.

From a practical viewpoint, this experiment reconstructed part of mammalian MAPK pathway in an organism which is amenable for use in screening, eg for inhibitors of this pathway.

We have also shown that the Mos protein kinase can activate, MAPKK expressed in yeast. The c-mos gene was first identified as the cellular homologue of a transforming gene (v-mos) from a mouse retrovirus (54), and it was subsequently shown that c-mos can also transform mammalian cells. The c-mos gene product (Mos) is a serine/threonine kinase expressed in germ cells. Extensive studies have been done on Mos in Xenopus (frog) where was shown to be necessary for meiotic maturation of oocytes in response to progesterone.

Although Mos expression is generally confined to germ cells, it is possible that inappropriate expression of Mos could lead to oncogenesis through activation of the MAP kinase pathway. Indeed high level expression of Mos protein has been detected in cervical carcinoma-derived cell lines (Li et al., 1993). Inhibitors of Mos kinase could have therapeutic potential in tumours that express Mos.

Two published studies have suggested that Mos is involved in the activation of Xenopus MAPK during meiosis (56, 57). Furthermore, a bacterially expressed maltose-binding protein (MBP)-Mos fusion protein could activate purified, phosphatase-inactivated MAPKK, suggesting that Mos could be a MAPKKK (56). However, the MBP-Mos fusion protein had to be "activated" by incubation in a cell extract (rabbit reticulocyte lysate) so that it was difficult to eliminate the possibility that a MAPKKK in the reticulocyte lysate that associates with MBP-Mos was responsible for the in vitro activation of MAPKK, and not Mos itself.

The work described in Example 2 confirmed that Mos works in yeast in a manner similar to Raf-1, directly phosphorylating MAPKK, and so can be termed a MAPKK kinase or MAPKKK.

The full picture of how the MAP kinase pathway is switched off is as yet unclear. Down-regulation of MAP kinase activity by de-phosphorylation is likely to be of key importance. The human gene CL100 [41] and its murine homologue 3CH134 [42] were originally discovered as genes whose trascription was stimulated by growth factors, oxidative stress and heat shock. Subsequently, they were shown to encode polypeptides that have both serine/threonine and tyrosine phosphatase activity [43–44]. This removal of phosphate from both threonine and tyrosine on MAP kinase is unusual. When expressed in vitro [43–44] this gene product has been shown to be very specific for MAP kinase and leads to its inactivation. Co-expression of the murine gene 3CH134 and the erk2 MAP kinase isoform in mammalian cells leads to the dephosphorylation and inactivation of the MAP kinase [45]

Disclosed herein are several new genes, each encoding a polypeptide implicated in the MAP kinase regulatory system.

Several nucleic acid molecules have been discovered and isolated encoding proteins which are related to the known MAP kinase phosphatases. Using insight gained from specialist knowledge in the field, an investigative procedure was designed which resulted in the obtention of the new genes. The actual procedure used is described in detail below, and disclosed, along with the phosphatases, in. patent application GB 9402573.1.

The sequences of the polypeptides encoded by the novel nucleic acid sequences share a degree of homology with the sequence of the known MAP kinase phosphatase, CL100, which is sufficient for indication as phosphatases, particularly MAP kinase phosphatases.

MAP kinase phosphatases are likely to act as off switches for cell proliferation. The fact that there are multiple MAP kinase phosphatases suggests that there may be some specificity to the off switches. Activators of the MAP kinase phosphatases, either general or for specific family members, may be anti-proliferative agents. Provision of nucleic acid encoding phosphatases enables screening for such activators. Loss of MAP kinase phosphatase activity by, for example, mutation may lead to uncontrolled cell proliferation. Hence, some of these genes may prove to be tumour suppressor genes.

According to a first aspect of the present invention there is provided a method of screening for a substance which is an inhibitor of mammalian MAPK pathway, which comprises:
  taking yeast which is deficient for yeast MAPKK kinase and MAPKK gene activity, and wherein the deficiency is complemented by coexpression of mammalian MAPKK kinase and MAPKK genes;
  exposing the yeast to a test substance under conditions which would normally lead to the activation of the yeast MAPK pathway; and
  looking for an end point indicative of activation of the yeast MAPK pathway;
    whereby inhibition of that endpoint indicates inhibition of the MAPK pathway by the test substance.

According to a second aspect of the present invention there is provided a method of screening for a substance which is an inhibitor of mammalian MAPK phosphatase action on MAPK, which comprises:
  taking a yeast which is deficient for MAPKK kinase and/or MAPKK gene activity, wherein the deficiency is complemented by coexpression of mammalian MAPKK kinase and MAPKK genes and wherein a mammalian MAPK phosphatase gene is expressible;
  exposing the yeast to a test substance under conditions wherein the MAPK phosphatase normally inhibits the yeast MAPK pathway; and looking for an end point indicative of activation of the yeast MAPK pathway;
    whereby activation of that endpoint indicates inhibition of MAPK phosphatase action on the MAPK by the test substance.

According to a third aspect of the present invention there is provided a method of screening for a substance which affects mammalian MAPK phosphatase action on mammalian MAPK pathway which comprises:
  taking a yeast which is deficient for MAPKK. kinase and/or MAPK gene activity, wherein the deficiency is complemented by coexpression of mammalian MAPKK kinase and MAPKK genes and wherein a mammalian MAPK phosphatase gene is expressible;
  exposing the yeast to a test substance under conditions wherein the MAPK phosphatase is expressed and normally partially inhibits the yeast MAPK pathway; and looking for an end point indicative of activation or further inhibition of the yeast MAPK pathway;
    whereby activation of that endpoint indicates inhibition of MAPK phosphatase action by the test substance, and further inhibition of that endpoint indicates either activation of MAPK phosphatase action by the test substance or inhibition of the MAPK pathway by the test substance.

The yeast may be any strain of *Schizosaccharomyces pombe, Saccharomyces cerevisiae*, (eg *Saccharomyces carlsbergensis*), or *Candida albicans*, though the asexual nature of this last yeast, and the fact that it is diploid, make mutation and selection more difficult. A MAPK homologue has been stored from *Candida albicans* (58). In *Schizosaccharomyces pombe* the MAPKK kinase and MAPKK may be Byr1 and Byr2 respectively. In *Saccharomyces cerevisiae* they may be STE7 and STE11 in the FUS3/KSS1 pathway or equivalents in other MAPK pathways, as discussed supra.

Neiman et al (52) demonstrated interchangeability of *S. pombe* genes byr2, byr1 and spk1 with *S. cerevisiae* genes STE11, STE7 and FUS3. Mutations in one species can be complemented by expression of the equivalent genes from the other, illustrating the conservation of function of the kinases between the species.

The yeast MAP kinase gene (eg spk1) may be replaced by a mammalian MAPK gene able to function in the yeast environment. This may be particularly desirable when substances are to be tested for effect on MAP kinase phosphatase action of MAPK pathway. Neiman et al (52) demonstrated that the mammalian MAP kinase ERK2 can function in place of spk1 in *S. pombe*. Likewise, Gotoh et al (19) demonstrated that Xenopus MAPK can act in *S. pombe* in place of spk1. Yeast components upstream of MAPKK kinase, eg Ras, may also be replaced by a mammalian homologue.

The end point of the screen may be the mating ability of the yeast or the ability to sporulate, or it can be an artificially constructed end point obtained by making an activated component such as Spk1 or MAPK switch on a reporter gene, in known manner. For instance, a reporter for Spk1 activation may be the promoter of a gene that is regulated by the ras-spk1 pathway in response to mating pheromones, such as matpm (65) or sxa2 (66), fused to a reporter gene such as lacZ encoding β-galactosidase. A suitable reporter system for mammalian MAPK activation may be based on phosphorylation by MAPK activating a GAL4-Elk-1 fusion protein, which acts as a transcription factor to stimulate expression from a GAL4 operator. If the GAL4 operator is fused to a reporter gene, such as lacZ, and incorporated into the yeast, there will be a detectable end-point.

The reporter gene is likely to encode an enzyme which catalyses a reaction which produces a visually detectable signal, such as a coloured product. Many examples are known, including β-galactosidase and luciferase. β-galactosidase activity can be assayed by production of blue colour on substrate, the assay being visual or by use of a spectrophotometer to measure absorbance. Fluorescence, eg that produced as a result of luciferase activity, can be quantitated using a spectrophotometer. Radioactive assays may be used, for instance using chloramphenicol acetyltransferase, which may also be used in non-radioactive assays. Spontaneous fluorescence, such as that of green fluorescent protein disclosed by Chalfie et al (60), may be used. The product of activity of a reporter gene may be assayed, to determine gene activity, using a specific binding pair member able to bind the product, eg. an antibody.

The MAPKK kinase may be Raf, Mos, MEK kinase (Lange-Carter et al 1993) or any other mammalian protein which can activate MAPKK by phosphorylation.

Variants, mutants or derivatives of a wild-type MAPKK kinase, (eg raf or mos) MAPKK, MAPK or MAPK phosphatase gene may be used. Variants and mutants have some change to the wild-type nucleic acid sequence. The change may be one or more of insertion, deletion or substitution of one or more nucleotides resulting in either no change of amino acid sequence of the encoded protein or a change affecting one or more amino acid residues in the encoded protein, which may or may not affect the protein function. The methods of the present invention enable testing of mutants, variants or derivatives which are naturally occuring or created artificially in vitro. This is likely to broaden the range of useful activators or inhibitors of elements of the MAPK pathway, such as MAPK phosphatases, which can be found using the present invention.

Following identification of a substance which affects components of the pathway, an inhibitor of MAPK, an inhibtor or activator of MAPK phosphatase and so on, the substance may be manufactured or used, for instance in the preparation of a medicament. Such a medicament may particularly be for treatment of a proliferative disorder (eg cancer) in a mammal, or treatment of other disorders where MAP kinases may be implicated, such as inflammatory disorders (63), cardiovascular disorders (64) and neurological disease (22) (Nerve Growth Factor activates a MAPK cascade.) The manufacture and/or use of a substance identified using the present invention fall within the scope of the invention.

Additionally, the present invention extends to a substance identified by a method according to the invention as an inhibitor of mammalian MAPK pathway, or as a substance which affects mammalian MAPK phosphatase action on MAPK (eg an activator or inhibitor of this action), for use as a pharmaceutical, and the use of such substances in the preparation of a medicament for the treatment of any one or more of a proliferative disorder, an inflammatory disorder, a cardiovascular disorder and a neurological disorder.

According to another aspect of the present invention there is provided yeast which is defective in yeast MAPKK kinase and/or MAPKK gene activity, which defect is complemented by the coexpression of mammalian MAPKK kinase and MAPKK genes. The yeast may be *Schizosaccharomyces pombe* (byr1 and/or byr2 gene activity may be defective) *Saccharomyces cerevisiae* (in which case the defective genes may be STE7 and/or STE11, or the equivalents in another MAPK pathway), or *Candida albicans*. (For further discussion of this see supra.) The yeast MAPK (eg Spk1) may also be replaced by a mammalian MAPK, and means for assessing MAPK activity designed accordingly (ie the end-point for the screening methods according to the invention). Upstream components of a subject pathway (eg Ras) may also be replaced with a mammalian homologue.

A number of mammalian MAPK pathways are known to exist. It may be that in a particular case a factor found in mammalian cells but not in yeast is required for activity of one of the components of a pathway e.g. MAPKKK, MAPKK, MAPK. Then, if that particular component is to be used in one of the screening methods of the invention, either the factor will have to be introduced into the yeast, eg by cloning the gene encoding the factor and introducing it into the yeast so that the factor is expressed, or by mutating the component in a way which removes its requirement for the factor. (Raf-1, as an illustration, can be activated by deletion of an N-terminal domain.)

The yeast may further contain nucleic acid from which a mammalian MAPK phosphatase is expressible, to enable screening for substances which interfere with the action of MAPK phosphatase on MAPK, mammalian or yeast, (Spk1, FUS3, KSS1, HOG1 or MPK1, etc). The MAPK phosphatase may be CL100, 3CH134 or any of the phosphatases made available herein. Sequence information is given in the figures (SEQ ID NOS:5–24). As already discussed, the phosphatase may be a variant, mutant or derivative of the wild-type.

Preferably, the mammalian MAPK phosphatase is overexpressed, ie expressed at a level which is high enough to mask any effect of yeast phosphatases on Spk1 or mammalian MAPK (if present in place of Spk1) in a screening method according to the invention. It may be desirable in certain circumstances to disrupt a yeast phosphatase gene function to stop or reduce any interfering action the yeast phosphatase might otherwise have on screening for substances which affect mammalian MAPK phosphatase action. For instance, if the mammalian phosphatase is not overexpressed but is expressed at a relatively low level, it may be that endogenous yeast phosphatase will act on the MAPK in the yeast to an extent that any effect (activation or inhibition) of the test substance on the mammalian phosphatase action on MAPK is not detectable.

Techniques for disrupting gene function are known and facilitated by the fact that a *Saccharomyces cerevisiae* gene encoding a phosphatase which acts on FUS3/KSS1 has been cloned (59). A combination of in vitro mutagenesis and homologous recombination may be used to disrupt this gene's function. Furthermore, other phosphatase genes in yeast are likely to have sequences homologous to this gene and so may be cloned using primers or probes with sequences based on parts of the cloned gene, then mutated or disrupted in some way before being used to replace the wild-type gene in a yeast chromosome.

The yeast according to the present invention are useful in the methods described herein for the identification of useful substances.

The mammalian genes may be introduced into yeast on autonomously replicating plasmids and propagated as extrachromosomal elements as illustrated herein. These vector plasmids, known as shuttle-vectors, contain sequences for replication and selection both in bacteria and yeast [46]. Other controlling elements such as promoter sequences and transcription termination sequences are included for expression of the mammalian genes. [47–48]. The controlling elements may be derived from yeast or from other organisms or viruses.

Alternatively the mammalian genes may be introduced into the yeast genome. This may be achieved by random, non-homologous recombination or by homologous recombination directed by cloned yeast sequences into a predetermined site in the chromosome [49]. Expression of the mammalian genes would be regulated by controlling elements like those used in plasmid vectors. Different promoter sequences may be used to vary the level of expression of the mammalian gene products [50].

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press.

The methods of the present invention will identify substances which interfere with the activity of a component in the pathway or which interfere with the interaction of two or more components which each other. The functioning of any enzymatic cascade depends on both enzymatic activity of each component and the ability of each component to interact with another component.

The experimental basis for the invention and illustrative embodiments of the invention will now be described in more detail, with reference to the accompanying drawings. All publications mentioned in the text are incorporated herein by reference.

FIGS. 1a–1f show complementation of the mating defect of a byr1 mutant by coexpression of Raf and MAPKK. Micrographs of a byr1 mutant transformed with MAPKK alone (a), MAPKK plus raf-1 (b), MAPKK plus Δraf-1. (c), raf-1 alone (d), Δraf-1 alone (e), and *S. pombe* byr1⁺ (f).

Figure 2A:
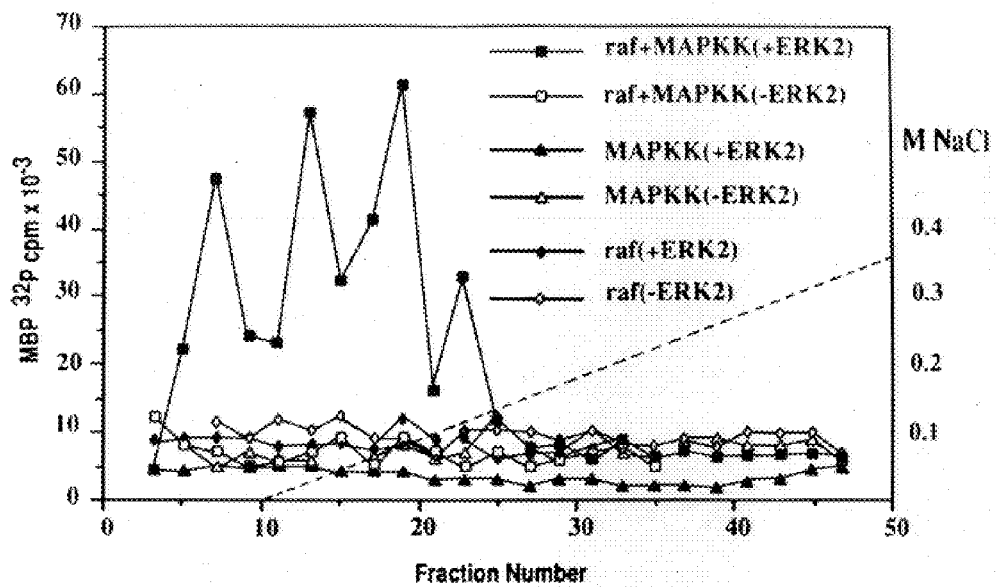
Figure 2B:
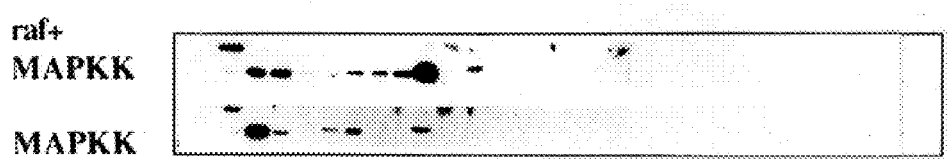

FIGS. 2A–2B show MAPKK activity in *S. pombe* cells coexpressing Raf. A; MAPKK and MAPK activities of fractionated cell extracts from a byr1 mutant strain (CB53) transformed with MAPKK and Δraf-1. B; Immunoblot of column fractions to detect rabbit MAPKK.

Figure 3A:
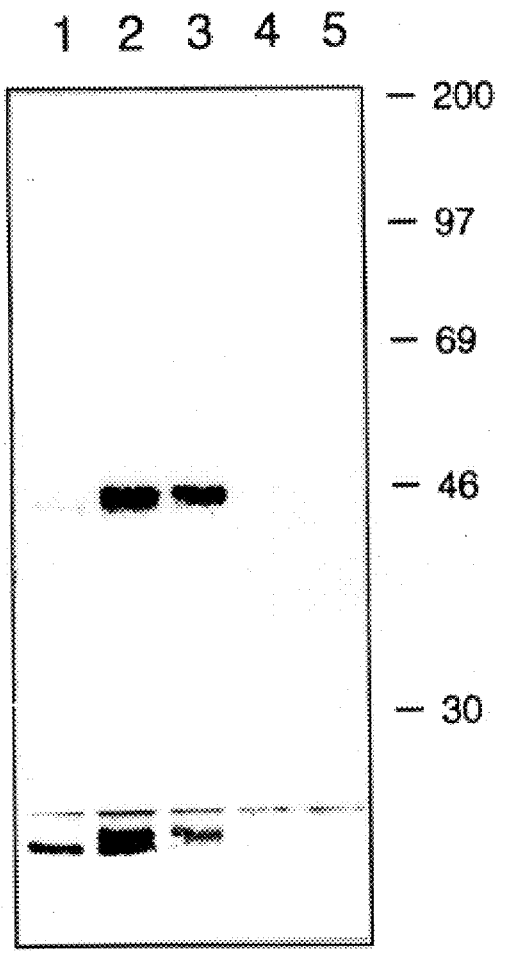
Figure 3B:
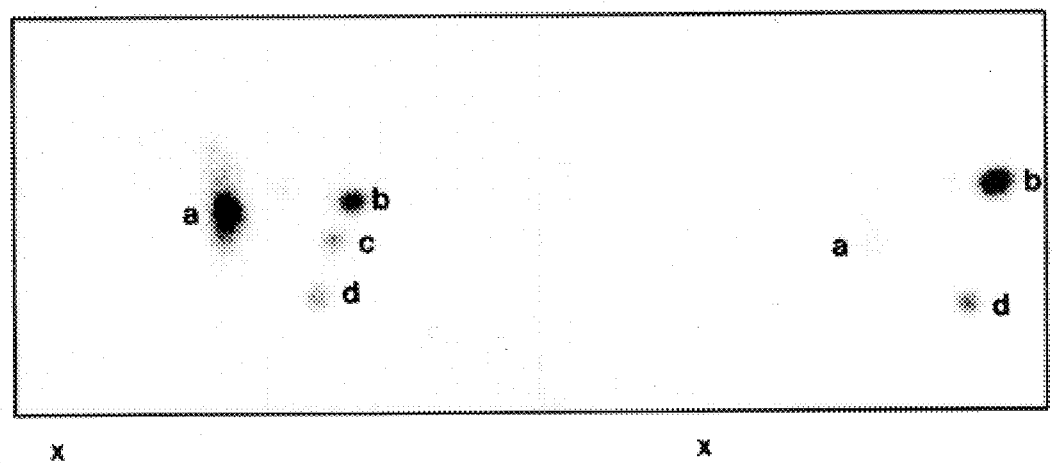

FIGS. 3A–3B show stimulation of MAPKK phosphorylation by raf in *S. pombe*. A; Immunoprecipitation of rabbit MAPKK in cells expressing MAPKK alone (lane 1), MAPKK plus raf-1 (lane 2), MAPKK plus Δraf-1 (lane 3), raf-1 alone (lane 4) and Δraf-1 alone (lane 5). Top: phosphor imager print showing phosphate-labelled MAPKK (lanes 1–3). Bottom: immunoblot of the same immunoprecipitated samples with the anti-MAPKK serum. B: Phosphopeptide maps of MAPKK. The origin is marked with a cross (bottom left of each panel). The horizontal dimension is electrophoresis (cathode to right) and the vertical dimension is chromatography.

FIGS. 4a–4h show complementation of the mating defect of byr1 of byr2 mutants by coexpression of mammalian MAPKK and Mos. (a) to (d), byr1 mutant transformed with either MAPKK alone (a), MAPKK and Mos (b), Mos alone (c), or byr1+ (d), (e) to (h), byr2 mutant transformed with either MAPKK alone (e), MAPKK and Mos (f), Mos alone (g), or byr2+ (h). METHODS. Mouse c-mos cDNA was cloned into pREP52, a derivative of pREP42 (Basi et al., 1993). The byr2 mutant strain CB85 (h$^{90}$byr2::ura4ΔRS ade6 leu1 ura4) was derived from JX3 (Gotoh et al., 1993). The other plasmids and the byr1 mutant strain CB53 have been described previously (Hughes et al., 1993). The transformants were photographed after 3 days on synthetic sporulation agar (SSA).

Figure 5:
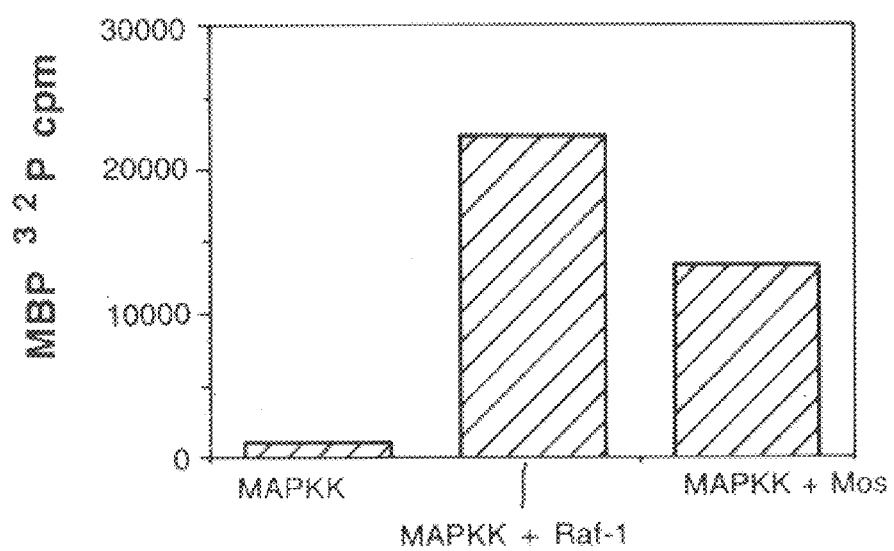

FIG. 5 shows MAPK kinase activity in a byr1 mutant expressing MAPKK and Mos. Cell extracts were prepared from a byr1 mutant strain (CB53) expressing either MAPKK alone, MAPKK and Raf-1, or MAPKK and Mos 5 μg of total protein from each extract was assayed for MAPKK activity as described previously (Hughes et al., 1993). Expression of each of the kinases in the extracts was confirmed by immunoblot analysis (data not shown).

FIGS. 6a–6i show DNA sequences of novel phosphatase molecules (SEQ ID NOS:5–13). STY2–STY4 are PCR products amplified from RNA produced form A431 (SEQ ID NOS:5–7) cells as described in the text. STY6 (SEQ ID NO:9) is part of a cDNA clone isolated by screening a human liver cDNA library with a mixture of STY2 and STY3 probes shown in part a) and b). STY7–STY10 (SEQ ID NOS:10–13) are parts of cDNA clones isolated by screening a human brain cDNA library with a mixture of STY2 and STY3 probes shown in part a) and b). All sequences apart from STY7 (SEQ ID NO:10) and STY10 (SEQ ID NO:13) show homology to CL100. In the case of these clones the sequence shown does not show homology to CL100 but the cDNA clones hybridised strongly to the STY2/3 probe suggesting that these clones also encode novel phosphatase genes. FIG. 6 (*a*) shows STY2 (SEQ ID NO:5), FIG. 6 (*b*) shows STY 3 (SEQ ID NO:6), FIG. 6 (*c*) shows STY4 (SEQ ID NO:7), FIG. 6 (*d*) shows STY 5 (SEQ ID NO:8), FIG. 6 (*e*) shows STY6 (SEQ ID NO:9), FIG. 6 (*f*) shows STY 7 (SEQ ID NO:10), FIG. 6 (*g*) shows STY 8 (SEQ ID NO:11), FIG. 6 (*h*) shows STY 9 (SEQ ID NO:12) and FIG. 6 (*i*) shows STY10(SEQ ID NO:13).

FIG. 7 shows deduced amino acid sequences of phosphatase clones aligned with the amino acid sequence of CL100. For parts a)–c) spaces indicate residues that are identical with CL100 (SEQ ID NOS:14, 19 and 21 respectively) and dots indicate residues which have not yet been determined. For part d) which is a comparison of the full length clone for STY8 (SEQ ID NO:23) with CL100 (SEQ ID NO:24) Dashes (-) indicate gaps introduced into the sequences to optimise their alignment. Shaded residues correspond to residues that are identical between STY8 and CL100.

The amino acid sequences shown correspond to residues 177–255 of STY2 (SEQ ID NO:15), STY3 (SEQ ID NO:16), STY4 (SEQ ID NO:17) and STY5 (SEQ ID NO:18) for FIG. 7 (*a*), 231–302 of STY6 (SEQ ID NO:20) for FIG. 7(*b*), 223–267 of STY9 (SEQ ID NO:22) for FIG. 7 (*c*) and 1–367 of STY8 (SEQ ID NO:23) for FIG. 7 (*d*).

Figure 8:
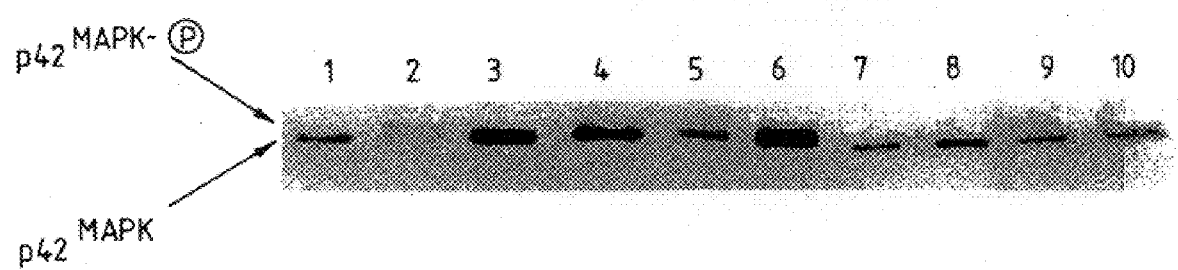

FIG. 8 shows proof that STY8 encodes MAP kinase phosphatase activity. Protein extracts were prepared from COS cells transfected with various recombinant plasmids before or after stimulation of the cells with EGF. These extracts were electrophoresed on SDS/polyacrylamide gels and the proteins then transferred to a nitrocellulose membrane. This membrane was then incubated with the anti-myc antibody 9E10, treated by the ECL procedure and the resulting chemiluminescence detected on xray film. It can be seen that in the absence of stimulatory ligand (EGF) the anti-myc antibody 9E10 reveals only a single band of MAP kinase on western blotting (lane 1). In the presence of EGF (lane 2) a clear doublet of bands is present indicating the partial phosphorylation of the MAP kinase. This is unaffected by expression of the parental expression vector (lanes 3 and 4). However, expression of CL100 or STY8 in the presence of EGF (lanes 7–10) leads to abolition of the EGF induced shift indicating that both these molecules encode MAP kinase phosphatases. Lanes 5 and 6 in which the cells are transfected with Myc-tagged STY8 shows that the STY8 protein is indeed expressed. Lane 1 is MAPK; Lane 2 is MAPK+EGF; Lane 3 is MAPK+pMT; Lane 4 is MAPK+pMT+EGF; Lane 5 is Myc–STY8; Lane 6 is Myc–STY8+EGF; Lane 7 is MAPK+CL100; Lane 8 is MAPK+CL100+EGF; Lane 9 is MAPK+STY8; Lane 10 is MAPK+STY8+EGF.

EXAMPLE 1

Referring firstly to FIG. 1; rabbit MAPKK cDNA and *S. pombe* byr1$^+$ were cloned into pREP41 and human raft-1 and Δraf-1 were cloned into pREP42. The raf-1 clone encodes the full length Raf-1 protein whereas in Δraf-1 the first 324 amino acids are detected (7). The vector plasmids are derivatives of the nmt1 promoter plasmids[29] and carry either the *S. cerevisiae* LEU2 gene (pREP41) or the *S. pombe* ura4$^+$ gene (pREP42) as selectable markers[30]. A null mutant of byr1, with a 0.18-kilobase deletion (SpeI to BamHI) of the open reading frame, was constructed by one-step gene disruption. The byr1 mutant strain CB53 (h$^9$ byr1::ura4ΔRA ade6 leu1 ura4) was transformed with two plasmids, one derived from pREP41 and the other from pREP42, and Leu$^+$ Ura$^+$ transformants carrying both plasmids were selected. Transformants were grown on synthetic sporulation agar (SSA)[31] for 3 days and then photographed. Molecular genetics methods for *S. pombe* were as described[32,33].

Referring to FIG. 2; cells were grown in minimal medium (EMM) to ca 1×10$^7$ cells/ml, harvested by centrifugation and washed in stop buffer (150 mM NaCl, 50 mM NaF, 10 mM EDTA, 1 mM NaN$_3$, pH 8.0). Cells (2.0×10$^8$) suspended in 20 μl 50 mM Tris. Cl pH 7.3, 40 mM Na$_4$P$_2$O$_7$, 50 mM NaF, 5 mM MgCl$_2$, 0.3 mM Na orthovanadate, 10 mM EGTA, 1% Triton X-100, 20 μg/ml leupeptin, 20 μg/ml aprotinin, 1 mM PMSF were broken with 1 g glass beads by vortexing for 2 min, the beads washed with 50 volumes of buffer A (50 mM Tris.Cl pH 7.0, 2 mM EDTA, 2 mM EGTA, 0.1% β-mercaptoethanol, 5% glycerol, 0.03% Brij35, 0.3 mM Na orthovanadate, 1 mM benzamidine, 4 μg/ml leupeptin) and the lysate cleared by centrifugation in an Eppendorf microcentrifuge at 14,000 rpm for 10 min; 0.5 ml cleared lysate (1.5 mg total protein) was then applied to a 1 ml Mono-Q column (Pharmacia L. K. B.) and the column developed in buffer A with a 25 ml linear salt gradient to 0.35 M NaCl. The flow rate was 1 ml min-1 and 0.5 ml fractions were collected and assayed for myelin basic protein (MBP) kinase activity after preincubation with recombinant ERK2 (+ERK2) for MAPKK activity or after preincubation with buffer (-ERK2) for MAPK activity, essentially as described by Traverse et al[24].

(B) Aliquots of each fraction assayed for kinase activity were resolved by 10% SDS-PAGE, electroblotted to Immobilon (Millipore) and probed with rabbit polyclonal antibody 179 raised against a GST-rabbit MAPKK fusion protein (A. Ashworth and C. J. Marshall, unpublished) and ECL reagents (Amersham).

Referring to FIG. 3; cells were grown in low-phosphate EMM to mid log phase (ca 5×10$^6$ cells/ml), labelled with [$^{32}$P] orthophosphate for 3.5 h[32] and then broken with glass beads in lysis buffer (25 mM Tris.Cl pH 8.0, 40 mM Na$_4$P$_2$O$_7$, 50 mM NaF, 5 mM MgCl$_2$, 0.1 mM Na orthovanadate, 10 mM EGTA, 1% Triton X-100, protease inhibitors: 20 μg/ml aprotinin, 20 μg/ml leupeptin, 1 mM PMSF). After centrifugation (15,000 rpm for 15 mins) the supernatants were adjusted to 0.5% sodium deoxycholate (Na DOC), 0.1% sodium dodecyl sulphate (SDS), and incubated for 1 h with anti MAPKK serum 179 precoupled to protein A-sepharose. The beads were washed four times with buffer (lysis buffer with Na DOC and SDS, without MgCl$_2$ and protease inhibitors), incubated with 0.1 mg/ml RNase for 30 minutes, washed again, suspended in Laemmli's sample buffer and boiled. Samples were resolved by 10% SDS-PAGE and electroblotted to Immobilon. After autoradiography MAPK was detected using the anti-MAPKK serum 179 and alkaline-phosphatase-conjugated secondary antibody (Promega). Radioactivity was quantitated using a phosphorimager (Molecular Dynamics) and the immunoblot was scanned on a scanning densitometer (Joyce-Loebl). Two-dimensional phosphopeptide maps were obtained after trypsin digestion of MAPKK on Immobilon. The first dimension was electrophoresis in pH 1.9 buffer at 400 V for 60 min on cellulose thin-layer plates (Kodak); the second dimension was ascending chromatography developed with phosphochromatography buffer for 3 h[34].

DISCUSSION

Mammalian MAP kinase kinases (MAPKKs) are structurally related to the byr1 gene product of the fission yeast *S. pombe*. Rabbit MAPKK, for example, is 55% identical in amino-acid sequence to Byr1 in the catalytic domain and 38% identical overall. To see whether mammalian MAPKK might be able to complement the byr1 mutant defect, a rabbit MAPKK cDNA driven by a fission yeast promoter was transformed into a byr1 mutant strain. Expression of MAPKK could not complement the mating defect of this strain (FIG. 1). Since MAPKK must be activated by phosphorylation[22], it was possible that *S. pombe* did not have such an activator. The product of the raf-1 protooncogene has been implicated in activation of the MAP kinase pathway in mammalian cells, perhaps as a direct activator of MAPKK[6–8], so we examined whether Raf-1 could activate MAPKK in *S. pombe*. When byr1 mutant cells coexpressed either Raf-1 or ΔRaf-1, an activated derivative of Raf-1, together with MAPKK they were able to mate (FIG. 1), although the mating frequency was lower than that of cells carrying the wild-type byr1$^+$ gene (Table 1). Expression of Raf-1 or ΔRaf-1 alone or MAPKK alone did not allow byr1 mutant cells to mate, showing that expression of both MAPKK and Raf is required to substitute for Byr1.

The *S. pombe* gene spk7, encodes a protein kinase thought to be involved in the same pathway as Byr1[9,19]. The Spk1 kinase is homologous to vertebrate MAP kinases and to *S. cerevisiae* FUS3 and KSS1 and like them contains the regulatory TEY phosphorylation site motif in subdomain VIII[9]. Coincident with the work we describe here, others have shown that Xenopus and mammalian MAPK's can act in place of Spk1 in *S. pombe*[19], (52). By analogy to other systems[21,23] and from genetic and biochemical analysis[19] it is probable that Byr1 phosphorylates and activates Spk1. Thus activated MAPKK may be substituting for Byr1 by phosphorylating and activating the Spk1 kinase in *S. pombe*. Consistent with this hypothesis, coexpression of MAPKK and Raf could not rescue the mating deficiency of a spk1 null mutant (Table 1).

These experiments show that mammalian MAPKK can function in *S. pombe* with coexpression of Raf. To investigate whether the kinase activity of MAPKK was dependent on Raf, cell extracts were prepared from *S. pombe* cells expressing MAPKK alone, MAPKK plus ΔRaf-1 or ΔRaf-1 alone, fractionated on a Mono Q (trade mark) ion exchange column and the fractions assayed for MAP kinase activity or MAP kinase activity (FIG. 2). MAPKK activity was detectable only in cells coexpressing MAPKK and ΔRaf-1. Immunoblot analysis of total cell extracts showed that expression of ΔRaf-1 did not affect the level of expression of MAPKK. The elution pattern of active MAPKK from the Mono Q column was complex with four peaks of activity that correlated well with MAPKK in immunoblots (FIG. 2B). In cells expressing ΔRaf-1 the peak of MAPKK immunoreactivity eluted at ca 100 mM NaCl (fraction 19) which corresponded to the most active fraction and is similar to the position of the major peak of MAPKK activity from mammalian cells[24]. In the absence of Raf, most of the MAPKK was found in the column flow-through fractions (FIG. 2B). No MAP kinase activity could be detected in any of the extracts.

The elution pattern of active MAPKK suggested some modification of the protein in cells expressing Raf. Since Raf-1 is a protein kinase we looked at the phosphorylation state of MAPKK in S. pombe after metabolic labelling with $^{32}$P-orthophosphate. Although MAPKK was phosphorylated in the absence of Raf-1, coexpression of Raf-1 or ΔRaf-1 led to hyperphosphorylation of MAPKK which was accompanied by a decrease in its mobility upon gel electrophoresis (FIGS. 2 and 3). We estimated that Raf-1 stimulated MAPKK phosphorylation about 4-fold and that ΔRaf-1 gave at least a 5-fold stimulation. In Raf-1 expressing cells the two forms of MAPKK were present in similar amounts while in ΔRaf-1 expressing cells the slower migrating form predominated (FIG. 3). Given that ΔRaf-1 is more effective than Raf-1 in activating MAPKK as judged by complementation of byr1 (Table 1) the slower migrating, hyperphosphorylated form of MAPKK is likely to be the biochemically active form. Phosphoamino acid analysis showed that hyperphosphorylated MAPKK contained phosphoserine and phosphothreonine but no phosphotyrosine (data not shown) in agreement with studies on active MAPKK from Xenopus oocytes[25].

The hyperphosphorylation of MAPKK in cells expressing Raf could be the result of phosphorylation on new sites, enhanced phosphorylation on the sites phosphorylated in the absence of Raf, or a combination of both mechanisms. To investigate MAPKK phosphorylation in more detail, tryptic phosphopeptide maps of immunoprecipitated MAPKK were generated (FIG. 3). The maps from Raf-1 :and ΔRaf-1 expressing cells were identical but distinct from the map from cells expressing MAPKK alone (FIG. 3). The most heavily labelled phosphopeptide is peptide a in cells expressing ΔRaf-1 but peptide b in cells without Raf. Phosphopeptide c is only seen in cells expressing Raf kinase. MAPKK phosphorylation in the absence of Raf may be the result of autophosphorylation, which is known to occur in vitro[14], or to phosphorylation by an endogenous yeast kinase. Whatever the cause, this Raf-independent phosphorylation does not activate the enzyme. MAPKK phosphorylation in the absence of Raf could be the result of autophosphorylation, which is known to occur in vitro[14], or to phosphorylation by an endogenous yeast kinase. Whatever the cause, this Raf-independent phosphorylation does not activate the enzyme.

Immunoprecipitates of Raf kinase from mammalian cells have been shown to phosphorylate and reactivate phosphatase-treated homogenously pure MAPKK preparations[7] and bacterially expressed v-Raf can also reactivate partially purified MAPKK[8]; but these experiments do not rule out an intermediate between Raf and MAPKK[26]. However, the inability of S. pombe to activate MAPKK unless Raf is expressed, strongly suggests that Raf directly phosphorylates and activates MAPKK. We observe that coexpression of Raf and MAPKK, but not Raf alone, also suppresses the mating defect of byr2 (Table 1) which encodes a kinase thought to function upstream of Byr1[27,28]. The inability of Raf alone to suppress a mutant that contains an intact byr1 gene shows that Raf cannot activate Byr1. This provides a strong genetic argument that Raf directly phosphorylates and activates MAPKK since a putative intermediate would have to be able to activate mammalian MAPKK but not Byr1, its S. pombe homologue.

EXAMPLE 2

Figure 4:
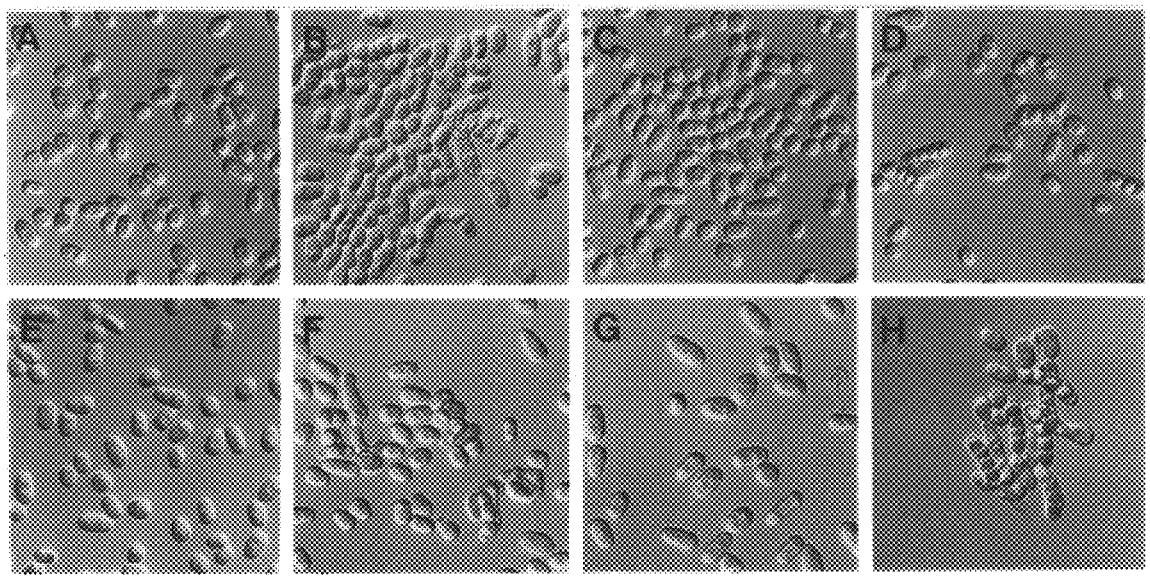

We coexpressed Mos and MAPKK in a S. pombe strain deficient in either byr1 or byr2 and found that the mating deficiency or the strains was rescued (FIG. 4). Expression of Mos itself had no effect on the mating ability of the S. pombe mutants.

Coexpression of Mos and MAPKK did not, however, restore mating to a strain defective in spk1, the S. pombe MAP kinase homologue (Table 2). These results with Mos and MAPKK are essentially identical to the findings with Raf-1 and MAPKK and strongly support the idea that Mos can directly activate MAPKK in vivo. To confirm that MAPKK was being activated in the presence of Mos we prepared cell extracts from byr1 mutant strains expressing the mammalian kinases and assayed them for MAPKK activity. The result shows that MAPKK is indeed activated when Mos is coexpressed (FIG. 5). Hyperphosphorylation of MAPKK when coexpressed with Mos was indicated by a decreased mobility of MAPKK in SDS-PAGE (data not shown). The ability of Mos to function as a MAPKKK when expressed in S. pombe contrasts with the inability of the MBP-Mos fusion protein purified from bacteria to activate MAPKK unless added to a mammalian cell extract (Posada et al., 1993). It seems likely that there is an endogenous component that can activate Mos kinase activity: the identity of the Mos activator(s) in mammalian cells and S. pombe is not known.

EXAMPLE 3

Isolation of MAP kinase phosphatase encoding genes

The human gene CL100 (3) and its murine homologue 3CH134 (42) have been shown to encode polypeptides that have both serine/threonine and tyrosine phosphatase activity (5,6). When expressed in vitro, the gene product has been shown to be very specific for MAP kinase and leads to its inactivation. Coexpression of the murine gene 3CH134 and the erk2 MAP kinase isoform in mammalian cells leads to the dephosphorylation and inactivation of the MAP kinase (7).

To identify related protein amino acids sequences human CL100 and its murine homologue 3CH134 and the human PAC-1 gene (42), a related T cell specific gene of unknown function, were compared. It proved possible to design degenerate PCR primers, based on conserved regions of the proteins. These primers were used to amplify related sequences from cDNA made from poly(A) $^+$RNA isolated from the human squamous cell line A431. A fragment of 270 bp was purified and subcloned. Of fifty individual clones sequences six proved to be identical to CL100. A further twelve clones were found to be homologous to, but distinguishable from, CL100:–STY2 isolated six times and STY3 four times, with single isolates of STY4 and STY5. In order to identify further related genes, we screened human brain and liver cDNA libraries with a mixed probe from STY2 and-3 PCR products. Several hybridising clones were analysed in more detail by restriction endonuclease maping and partial DNA sequencing. This resulted in the identification of several additional gene families, STY6–10, with STY1 being CL100. In total nine new genes were identified and these are compared to amino acid sequences of CL100, see FIG. 7. The high degree of similarity of these genes suggested that they encode proteins with MAP kinase phosphatase activity.

Cell Culture and RNA Preparation

A431 cells were grown in Dulbecco's modification of Eagle's minimal essential medium (DMEM) supplemented with 10% fetal calf serum. Total cellular RNA was prepared with RNAzolB(Promega) and poly(A)+RNA isolated with Dynabeads oligo(dT)25(Dynal).

Isolation of CL100-related cDNAs

Two degenerate oligonucleotides TA(T,C)GA(T,C)CA(A, G)GG(A,G,T)GG(T,C,G,A)CC(A,T)GT (A,G,T)GA (SEQ ID NO:1) and AT(G,C,T)CC(A,T)GC(T,C)TG(A,G)CA(A, G)TG(T,C,G,A)AC SEQ ID NO:23) were designed based on amino acid sequences, YDQGGPVE SEQ ID NO:3) and VHCQAGI SEQ ID NO:4) conserved between human and mouse CL100 and the human PAC-1 gene. A431 poly (A)-RNA (1 μg) was reverse transcribed with SuperScript reverse transcriptase (BRL-GIBCO) and subject to PCR on a Techne PHC-1 thermal cycler with these oligonucleotides (Ashworth, 1993) under the following conditions: 94° C. for 30 sec, 50° C., 30 sec, 72° C. 1 min. A 270 bp band was purified by agarose gel electrophoresis and subcloned into pBluescript.

Fifty individual subclones were sequenced and of these six proved to be CL100. Twelve others were found to be homologous to but not identical to CL100, and these were grouped as four different potential phosphatases, designated STY2–STY5 with CL100 being STY1.

Structural Analysis of STY cDNAs

One of the cDNA clones isolated from the human brain is full length. Colinear alignments of the STY genes with CL100 show that amino acids around the highly conserved catalytic domain differ, and two conserved regions between CL100 and cdc25 are also present in STY8. Studies on the genomic structure of 3CH134 reveal that the transcription unit is 2.8 kbp long and split into four exons [46]. It will be of interest to elucidate the genomic structure of the STY genes, and determine if their promoter regions contain consensus sequences for transcription factors. Preliminary studies suggest that STY8 has a similar gene structure to 3CH134.

Functional Assays

The human CL100 and its murine counterpart 3CH134 function as immediate-early genes whose transcription is rapidly and transiently induced within minutes, with protein accumulation seen in the first hour upon growth factor stimulation [46,47]. As observed for the expression of several immediate-early genes, the rapid increase in growth factor receptor tyrosine kinase activity and subsequent activation of signalling molecules needs to return to normal levels to avoid abnormal growth. One method for accomplishing this implicates protein phosphatases whose expression is induced by external signals, such that they are present in the cell only under certain circumstances.

Evidence indicates that when CL100 and 3CH134 are expressed in vitro [48–50] or in vivo [47], the gene product leads to selective dephosphorylation of $p42^{mapk}$ blocking its activation by serum, oncogenic Ras, or activated Raf, whilst the catalytically inactive mutant of the phosphatase augments MAP kinase phosphorylation.

We tested whether the phosphatase STY8 exhibited similar specificity in vivo using a COS cell transient expression system. We cotransfected Cos cells with the reporter plasmid pEXV3-Myc-$p42^{mapk}$ together with various plasmids including pMT-Myc-STY8. FIG. 8 is typical of such an experiment.

It can be seen that in the absence of stimulatory ligand (EGF) the anti-myc antibody 9E10 reveals only a single band of MAP kinase on western blotting (lane 1). In the presence of EGF (lane 2) a clear doublet of bands is present indicating the partial phosphorylation of the MAP kinase. This is unaffected by expression of the parental expression vector (lanes 3 and 4). However expression of CL100 or STY8 in the presence of EGF (lanes 7–10) leads to abolition of the EGF induced shift indicating that both these molecules encode MAP kinase phosphatases. Lanes 5 and 6 in which the cells are transfected with Myc-tagged STY8 shows that the STY8 protein is indeed expressed.

The provision of the nucleic acid encoding MAP kinase phosphatases enables incorporation into a yeast screen as described, to look for activators and inhibitors of the MAP kinase pathway and investigate the interaction between various components, in particular MAP kinases and MAPK phosphatases.

EXAMPLE 4

Construction and use of a yeast strain for the identification of inhibitors of the MAP kinase pathway A S. pombe strain is constructed with the nmtl promoter-raf-1 cDNA-nmtl terminator (nmtl-raf) integrated at the byr2 locus in the chromosome. This is done by first cloning the nmtl-raf sequences into the coding region of the ura4+ gene such that the ura4 coding sequence is disrupted and non-functional to give ura4::nmtl-raf. This fragment is then transformed into a S. pombe strain carrying byr2 disrupted by ura4+ (byr2::ura4+; JX3, [19] and transformants resistant to 5-fluroorotic-acid (FOA), which selects against cells containing the normal ura4+ gene product, are selected. Some of the FOA resistant colonies will have the ura4+ gene at the byr2 locus replaced by homologous recombination with the disrupted ura4::nmtl-raf sequences. This strain now has nmtl-raf stably integrated within the disrupted byr2 gene (byr2::nmtl-raf). A second strain is constructed with the nmtl promoter-MAPKK cDNA-nmtl terminator (nmtl-MAPKK) integrated at the byr1 locus in the chromosome. This is done as described above for nmtl-raf except that the recipient strain has byr1::nmtl-MAPKK. The byr2::nmtl-raf and byr1::nmtl-MAPKK are crossed by protoplast fusion, the diploid sporulated and a double mutant strain (nmtl-raf/MAPKK) carrying both byr2::nmtl-raf and byr1::nmtl-MAPKK is identified by tetrad analysis.

A reporter construct consisting of the promoter sequence of the pheromone-induced gene matPm (which is induced by action of the MAPK pathway) upstream of the E. coli lacZ gene encoding β-galactosidase is then integrated by homologous recombination at the leu1 locus in the nmtl-raf/MAPKK strain to give the screening strain nmtl-raf/MAPKK/PM-lacZ. A control strain is produced by coupling a constitutive promoter adh1 to the lacZ gene and integrating this construct by homologous recombination into the yeast genome.

To identify substances that can inhibit the activity of Raf or MAPKK expressed in yeast the nmtl-raf/MAPKK/PM-lacZ strain and the control strain are exposed or not to the test substance. After a suitable period of time the activity of β-galactosidase in the exposed and non-exposed cultures is determined [51] and compared. Inhibition of β-galactosidase activity in the culture exposed to the substance identifies the substance as a candidate inhibitor of the mammalian protein kinases. The absence of an effect on β-galactosidase activity in the control strain rules out the possibility that the substance is an inhibitor of β-galactosidase.

EXAMPLE 5

Screening for inhibitors or activators of MAPK phosphatases (MKP) expressed in yeast A yeast strain is constructed as described above that carried nmt1-raf, nmt1-MAPKK, nmt1-MAPK, nmt1-MKP and matPm-lacZ integrated at the byr2, byr1, spk1, ade6 and leu1 loci, respectively. To identify substances that can alter the activity of the MKP the strain is exposed or not to the test substance and β-galactosidase activity is assayed as above. Increased β-galactosidase activity in the culture exposed to the test substance indicates possible inhibition of the MKP or activation of the protein kinases by the substance. Conversely, decreased β-galactosidase activity indicates possible activation of the MKP or inhibition of the protein kinases by the test substance.

SUMMARY

Intracellular signalling from receptor tyrosine kinases in mammalian cells has been shown to involve the activation of a signal cascade which includes $p21^{ras}$ and the protein kinases $p74^{raf-1}$, MAP kinase kinase and MAP kinases[1–8]. In the yeasts *S. pombe* and *S. cerevisiae* the response to mating pheromones utilises the Spk1 and KSS1/FUS3 kinases which have sequence homology to vertebrate MAP kinases[9–12]. The recent cloning of cDNAs for mammalian[13–15] and frog[16] MAP kinase kinases has shown that they are homologous to the *S. pombe* Byr1[17] and *S. cerevisiae* STE7[18] kinases which have been proposed to function upstream of spk1 and KSS1/FUS3 respectively[19–21]. We have demonstrated that mammalian proteins can substitute for components of the yeast pathway.

Expression of mammalian MAP kinase kinase alone fails to complement a byr1 mutant of *S. pombe*. When coexpressed with a MAPKK kinase, such as Raf or Mos, however, MAP kinase is activated by phosphorylation and the mating defect of byr1 mutant is rescued. This suggests that the pathways are functionally homologous and shows that the Raf and Mos kinases directly phosphorylate and activate MAP kinase kinase.

Yeast which are deficient in byr1 and/or byr2 activity and wherein the deficiency is complemented by coexpression of mammalian MAPKK kinase and MAPKK genes find use in methods of screening for compounds which interfere in one way or another with the MAPK pathway. MAPK phosphatase genes and/or mammalian MAPK can also be introduced into the yeast. Test substances can be screened to identify activators and inhibitors of various components. Activators and inhibitors identified in this way are potential therapeutics, useful in the fight against proliferative disorders. The invention provides valuable tools to those working in the field, facilitating the screening of substances and identifying those with potential.

TABLE 1

Cells were grown on sporulation agar (SSA) at 30° C. for 4 days and the number of zygotes, asci and unmated cells were counted. Two clones for each transformant were examined and the average mating frequency determined. Numbers in parentheses are the total number of cells counted for each transformant. The full genotypes of the mutant strains are CB53:h⁹⁰byr1::ura4ΔRS ade6 leu1 ura4; CB57:h⁹⁰ byr2-JM86 ade5 lev1 ura4. and CB57: h⁹⁰ spk1::ura4ΔRS ade6 leu1 ura4, which was derived from the spk1 mutant described in ref.9. The plasmids are described in the description of FIG. 1, except for the byr2 plasmid which has the byr2 gene cloned into pREP42 and the spk1 plasmid which is from ref. 9. ND, Not determined

TABLE 1

Mating frequency (%) of byr1, byr2 and spk1 mutants transformed with mammalian kinase genes

| | Mutant Strains | | |
|---|---|---|---|
| Plasmids | byr1Δ (CB53) | byr2 (CB59) | spk1Δ (CB57) |
| MAPKK | 0 (1362) | 0 (2177) | 0 (747) |
| MAPKK + raf-1 | 1.36 (736) | ND | 0 (854) |
| MAPKK + Δraf-1 | 3.30 (1755) | 4.30 (2045) | 0 (1050) |
| raf-1 | 0 (1574) | ND | ND |
| Δraf-1 | 0 (1538) | 0 (27601) | ND |
| MAPKK + byr2 | 0 (1708) | ND | ND |
| byr1 | 52.0 (477) | ND | ND |
| byr2 | ND | 25.1 (742) | ND |
| spk1 | ND | ND | 39.0 (267) |

TABLE 2

Complementation of *S. pombe* kinase mutants by mammalian Mos and MAPKK

| | Mutants | | |
|---|---|---|---|
| Plasmids | byr1Δ (CB53) | byr2Δ (CB85) | spk1Δ (CB57) |
| MAPKK | − | − | − |
| MAPKK + Mos | + | + | − |
| Mos | − | − | − |
| byr1+ | ++ | − | − |
| byr2+ | − | ++ | − |
| spk1+ | − | − | ++ |

The mating efficiency is shown as ++ (25 to 50%), + (1 to 5%) or − (less than 0.01%). Methods were as described previously (Hughes et al., 1993).

REFERENCES

1. Troppmair, J.,et al. Oncogene 7, 1867–1873 (1992).
2. Leevers, S. J. & Marshall, C. J. *EMBO J.* 11, 569–574 (1992).
3. Thomas, S. M., DeMarco, M., D'Arcangelo, G., Halegoua, S. & Brugge, J. S. *Cell* 68, 1031–1040 (1992).
4. Wood, K. W., Sarnecki, C., Roberts, T. M. & Blenis, J. *Cell* 68, 1041–1050 (1992).
5. de Vries Smits, A. M. M., Burgering, B. M. T., Leevers, S. J., Marshall, C. J. & Bos, J. L. *Nature* 357, 602–604 (1992).
6. Kyriakis, J. M., et al. *Nature* 358, 417–421 (1992).
7. Howe, L. R., et al. *Cell* 71, 335–342 (1992).
8. Dent, P., et al. *Science* 257, 1404–1407 (1992).
9. Toda, T., Shimanuki, M. & Yanagida, M. *Genes Dev.* 5, 60–73 (1991).
10. Courchesne, W. E., Kunisawa, R. & Thorner, *J. Cell* 58, 1107–1119 (1989).
11. Elion, E. A., Grisafi. P. L. & Fink, G. R. *Cell* 60, 649–664 (1990).
12. Elion, E. A., Brill, J. A. & Fink, G. R. *Proc. Natl. Acad. Sci. USA* 88, 9392–9396 (1991).
13. Ashworth, A., Nakielny, S. , Cohen, P. & Marshall, C. *Oncogene* 7, 2555–2556 (1992).
14 Crews, C. M., Alessandrini, A. & Erikson, R. *Science* 258, 478–480 (1992).

15. Seger, R. et al. *J. Biol. Chem.* 267, 25628–25631 (1993).
16. Kosako, H., Nishida, E. & Gotoh, Y. *EMBO J.* 12, 787–794 (1993).
17. Nadin-Davis, S. A. & Nasim, A. *EMBO J.* 7, 985–993 (1988).
18. Teague, M. A., Chaleff, D. T. & Errede. B. *Proc. Natl. Acad. Sci. USA* 83, 7371–7375 (1986).
19. Gotoh, Y. et al. *Molec. Cell. Biol.* in press (1993).
20. Gartner, A., Nasmyth, K. & Ammerer, G. *Genes Dev.* 6, 1280–1292 (1992).
21. Errede. B., Gartner, A., Zhou, Z., Nasmyth, K. & Ammerer, G. *Nature* 362, 261–265 (1993).
22. Gómez, N. & Cohen, P. *Nature* 353, 170–173 (1991).
23. Nakielny, S., Cohen, P., Wu, J. & Sturgill, T. W. *EMBO J.* 11, 2123–2129 (1992).
24. Traverse, S., Gómez, N., Paterson, H., Marshall, C. & Cohen, P. *Biochem.* 288, 351–355 (1992).23.
25 Matsuda, S., Gotoh, Y. & Nishida, E. *J. Biol. Chem.* 268, 3277–3281 (1993).
26. Roberts, T. M. *Nature* 360, 534 (1992).
27. Wang, Y., Xu, H. -P., Riggs, M., Rodgers, L. & Wigler, M. *Mol. Cell. Biol.* 11, 3554–3563 (1991).
28. Styrkarsdottir et al. *Mol. Gen. Genet* 235, 122–130 (1992).
29. Maundrell, K. *Gene* 123, 127–130 (1993).
30. Basi, G., Schmid, E. & Maundrell, K. *Gene* 123, 130–136 (1993).
31. Egel, R. *Planta* 98, 89–91 (1971).
32. Moreno, S., Klar, A. & Nurse, P. *Meth. Enzymol.* 194, 795–823 (1991).
33. Grimm, C., Kohli, J., Murray, J. & Maundrell, K. *Mol. Gen. Genet.* 215, 81–86 (1988).
34. Boyle, W. J., Van der Geer, P. & Hunter, T. *Meth. Enzymol,* 201, 110–149 (1991).
35. Yi, T. et al., *Mol. Cell. Biol.* 13, 7577–7586 (1993).
36. David, M. et al., *Mol. Cell. Biol.* 13, 7515–7521 (1993).
37. Tojo, A. et al., *Exp. Cell. Res.* 171, 16–23 (1987).
38. Klarlund, J. K. *Cell* 707–717 (1985).
39. Brown-Schimer, S. *Cancer Research* 52, 478–482 (1992).
40. Ramponi, P. Int. *J. Cancer* 51, 652–656 (1992).
41. Keyse, S. M. & Emslie, E. A. *Nature* 359, 644–647 (1992).
42. Charles, C. H., Abler, A. S. & Lau, L. F. *Oncogene* 7, 187–190 (1992).
43. Alessi, D. R., Smythe, C. & Keyse, S. M. *Oncogene* 8, 2015–2020 (1993).
44. Charles, C. H., Sun, H., Lau, L. F. & Tonks, N. K. *Proc. Natl. Acad. Sci.* 90, 5292–5296 (1993).
45. Sun, H., Charles, C. H., Lau, L. F. & Tonks, N. K. *Cell* 75, 487–493 (1993).
46. Strathern, J. N. & Higgins, D. R. *Methods Enzymol.* 194, 319–329 (1991).
47. Schneider, J. C. & Guarente, L. *Methods Enzymol.* 194, 373–388 (1991).
48. Maundrell, K. *Gene* 123, 127–130 (1993).
49. Rothstein, R. *Methods Enzymol.* 194, 281–301 (1991).
50. Forsburg, S. L. *Nucleic Acids Research* 21, 2955–2956 (1993).
51. Guarente, L. *Methods Enzymol.* 101, 181–191 (1983).
52. Neiman et al., *Molecular Biology of the Cell* 4, 107–120 (1993).
53. Ammerer, G. *Curr. Opin. Genet. Dev.* 4, 90–95 (1994).
54. Van Beveren, C., Galleshaw, J. A., Jonas, V., Berns, A. J. M., Doolittle, R. F., Donoghue, D. J. and Verma, I. M. *Nature* (London) 289, 258–262 (1981).
55. Li, C. -C. H., Chen, E., O'Connell, C. D. and Longo, D. L. *Oncogene* 8, 1685–1691 (1993).
56. Posada, J., Yew, N., Ahn, N. G., Vande Woude, G. F., and Cooper, J. A. *Mol. Cell. Biol.* 13, 2546–2553 (1993).
57. Nebrada, A. R., and Hunt, T. *EMBO J.* 12, 1979–1986 (1993).
58. Whiteway, M., Dignard, D. and Thomas, D. *Proc. Natl. Acad. Sci. USA* 89, 9410–9414 (1992).
59. Doi, K., Gartner, A., Ammerer, G., Errede, B., Shinkawa, H., Sugimoto, K. and Matsumoto, K. *EMBO J.* 13, 61–70 (1994).
60. Chalfie et al., *Science* 263, 802–805 (1994).
61. Pages, G., Lenormand, P., L'Allemain, Chambard, J., Meloche, S., Pouyssegur, J., (1993) *PNAS* 90:8319–8323
62. Marais, R., Wynne, J. and Treisman, R. (1993) *Cell* 73, 381–393
63. Guesdon, F., Freshney, N., Walker, R. J., Rawlinson, C. and Saklatvala, J. (1993) *J. Biol. Chem.* 268, 14343–14352
64. Bogoyevitch, M. A., Glennon, P.E., Andersson, M. B., Clerk, A., Lazou, A. Marshall, C. J., Parker, P. J. and Sugden, P. H. (1994) *J. Biol. Chem.* 269, 1110–1119
65. Nielson, O., Davey, J. and Egel, R. (1992) *EMBO J.* 11, 1391–1395
66. Imai, Y. Yamamoto, M. (1994) *Genes Dev.* 8,328–338

What is claimed is:

1. The method of screening for a substance which is an inhibitor of MAPK pathway, which comprises:
   taking yeast which is deficient for yeast MAPKK kinase and MAPKK gene activity, and wherein the deficiency is complemented by coexpression of a mammalian MAPKK kinase gene and a mammalian MAPKK gene;
   exposing the yeast to a test substance under conditions which would normally lead to the activation of the yeast MAPK pathway; and
   looking for an end point indicative of activation of the yeast MAPK pathway;
   whereby inhibition of that endpoint indicates inhibition of the MAPK pathway by the test substance.

2. The method according to claim 1 wherein the yeast is *Schizosaccharomyces pombe*.

3. The method according to claim 2 wherein the yeast MAPK pathway is the yeast Spk1 pathway.

4. The method according to claim 1 wherein the yeast is *Saccharomyces cerevisiae*.

5. The method according to claim 1 wherein the end point is ability of the yeast to mate, ability of the yeast to sporulate or a combination thereof.

6. The method according to claim 1 wherein the end point is production of a detectable substance whose production is mediated by the activation of MAPK.

7. The method according to claim 6 wherein the end point is expression of a reporter gene leading to a visually detectable signal.

8. The method according to claim 7 wherein the expression of the reporter gene gives rise to a coloured product.

9. The method according to claim 1 wherein one or both of said mammalian MAPKK kinase gene and said mammalian MAPKK gene is in mutant form.

10. The method according to claim 9 wherein the mammalian MAPKK kinase gene is in mutant form.

11. The method according to claim 10 wherein the mammalian MAPKK kinase gene is a deletional mutant.

12. The method according to claim 1 wherein the mammalian MAPKK kinase is raf.

13. The method according to claim 1 wherein the mammalian MAPKK kinase is mos.

14. The method according to claim 1, further comprising manufacturing of a mammalian MAPK pathway inhibitor obtained by said method.

15. The method according to claim 1, further comprising preparing of a medicament including a mammalian MAPK pathway inhibitor obtained by said method.

16. The method according to claim 15, wherein the medicament is for anti-proliferative treatment of a mammal.

17. A yeast which is defective in yeast MAPKK kinase gene activity, MAPKK gene activity, or a combination thereof, which defect is complemented by the coexpression of a mammalian MAPKK kinase gene and a mammalian MAPKK gene.

18. The yeast according to claim 17 which is derived from *Schizosaccharomyces pombe*.

19. The yeast according to claim 17 which is derived from *Saccharomyces cerevisiae*.

20. The yeast according to claim 17 containing nucleic acid from which a mammalian MAPK phosphatase is expressible.

21. The yeast according to claim 17 wherein mammalian MAPK substitutes for yeast MAPK.

22. A method of screening for a substance which is an inhibitor of MAPK phosphatase action on MAPK, which comprises:
   taking a yeast which is deficient for MAPKK kinase gene activity, MAPKK gene activity, or a combination thereof, wherein the deficiency is complemented by coexpression of a mammalian MAPKK kinase gene and a mammalian MAPKK gene and wherein a mammalian MAPK phosphatase gene is expressible;
   exposing the yeast to a test substance under conditions wherein the MAPK phosphatase normally inhibits the yeast MAPK pathway; and looking for an end point indicative of activation of the yeast MAPK pathway;
   whereby activation of that endpoint indicates inhibition of MAPK phosphatase action on the MAPK by the test substance.

23. The method according to claim 22, further comprising manufacturing of a mammalian MAPK phosphatase inhibitor obtained by said method.

24. The method according to claim 22, further comprising preparing of a medicament including a mammalian MAPK phosphatase inhibitor obtained by said method.

25. A method of screening for a substance which affects MAPK phosphatase action on MAPK pathway which comprises:
   taking a yeast which is deficient for MAPKK kinase gene activity, MAPKK gene activity, or a combination thereof, wherein the deficiency is complemented by coexpression of a mammalian MAPKK kinase gene and a mammalian MAPKK gene and wherein a mammalian MAPK phosphatase gene is expressible;

exposing the yeast to a test substance under conditions wherein the MAPK phosphatase is expressed and normally partially inhibits the yeast MAPK pathway; and looking for an end point indicative of activation or further inhibition of the yeast MAPK pathway;

whereby activation of that endpoint indicates inhibition of MAPK phosphatase action by the test substance, and further inhibition of that endpoint indicates either activation of MAPK phosphatase action by the test substance or inhibition of the MAPK pathway by the test substance.

26. The method according to claim 25, further comprising manufacturing of a mammalian MAPK phosphatase inhibitor or a mammalian MAPK phosphatase activator or a MAPK pathway inhibitor obtained by said method.

27. The method according to claim 25, further comprising preparing of a medicament including a mammalian MAPK phosphatase inhibitor or a mammalian MAPK phosphatase activator or a MAPK pathway inhibitor obtained by said method.

28. The method according to claim 22 or claim 25 wherein mammalian MAPK substitutes for yeast MAPK.

29. The method according to claim 22 or claim 25 wherein the yeast is *Schizosaccharomyces pombe.*

30. The method according to claim 22 or claim 25 wherein the yeast is *Saccharomyces cerevisiae.*

31. The method according to claim 22 or claim 25 wherein the end point is ability of the yeast to mate, ability of the yeast to sporulate or a combination thereof.

32. The method according to claim 22 or claim 25 wherein the end point is production of a detectable substance whose production is mediated by the activation of MAPK.

33. The method according to claim 32 wherein the end point is expression of a reporter gene leading to a visually detectable signal.

34. The method according to claim 33 wherein the expression of the reporter gene gives rise to a coloured product.

35. The method according to claim 22 or claim 25 wherein one or both of said mammalian MAPKK kinase gene and said mammalian MAPKK gene is in mutant form.

36. The method according to claim 35 wherein the mammalian MAPKK kinase gene is in mutant form.

37. The method according to claim 36 wherein the mammalian MAPKK kinase gene is a deletional mutant.

38. The method according to claim 22 or claim 25 wherein the mammalian MAPKK kinase is raf.

39. The method according to claim 22 or claim 25 wherein the mammalian MAPKK kinase is mos.

* * * * *